(12) United States Patent
Onishi

(10) Patent No.: US 9,890,398 B2
(45) Date of Patent: Feb. 13, 2018

(54) METHOD FOR PRODUCING ETHANOL USING RECOMBINANT YEAST

(71) Applicant: Toru Onishi, Toyota (JP)

(72) Inventor: Toru Onishi, Toyota (JP)

(73) Assignee: Toyota Jidosha Kabushiki Kaisha, Toyota-shi, Aichi (JP)

( * ) Notice: Subject to any disclaimer, the term of this patent is extended or adjusted under 35 U.S.C. 154(b) by 0 days.

(21) Appl. No.: 14/353,394

(22) PCT Filed: Oct. 23, 2012

(86) PCT No.: PCT/JP2012/077284
§ 371 (c)(1),
(2) Date: Apr. 22, 2014

(87) PCT Pub. No.: WO2013/061941
PCT Pub. Date: May 2, 2013

(65) Prior Publication Data
US 2014/0273136 A1    Sep. 18, 2014

(30) Foreign Application Priority Data

Oct. 24, 2011 (JP) .................... 2011-233300

(51) Int. Cl.
*C12P 7/14* (2006.01)
*C12N 9/02* (2006.01)
(Continued)

(52) U.S. Cl.
CPC .............. *C12P 7/14* (2013.01); *C12N 9/0008* (2013.01); *C12N 15/52* (2013.01); *C12P 7/10* (2013.01);
(Continued)

(58) Field of Classification Search
None
See application file for complete search history.

(56) References Cited

U.S. PATENT DOCUMENTS 8,772,012 B2    7/2014  Katahira et al.
8,795,998 B2    8/2014  Pronk et al.
(Continued)

FOREIGN PATENT DOCUMENTS

CN      102712895 A    10/2012
CN      102791858 A    11/2012
(Continued)

OTHER PUBLICATIONS

Oh et al., "Effects of overexpression of acetaldehyde dehydrogenase 6 and acetyl-CoA synthetase 1 on xylitol production in recombinant *Saccharomyces cerevisiae*", Biocatalysis and Agricultural Biotechnology, vol. 1, pp. 11-19, 2012 (available online Aug. 30, 2011).*
(Continued)

*Primary Examiner* — Richard Ekstrom
(74) *Attorney, Agent, or Firm* — Finnegan, Henderson, Farabow, Garrett & Dunner, LLP

(57) ABSTRACT

The invention is intended to metabolize acetic acid and to lower acetic acid concentration in a medium at the time of xylose assimilation and ethanol fermentation by a yeast strain having xylose-metabolizing ability. To this end, a recombinant yeast strain having xylose-metabolizing ability and comprising an acetaldehyde dehydrogenase gene introduced thereinto is cultured in a medium containing cellulose, cellulase, and xylose to perform ethanol fermentation.

3 Claims, 4 Drawing Sheets

(51) Int. Cl.
  *C12N 15/52* (2006.01)
  *C12P 7/10* (2006.01)
(52) U.S. Cl.
  CPC ......... *C12Y 102/0101* (2013.01); *Y02E 50/16* (2013.01); *Y02P 20/52* (2015.11)

(56) References Cited

U.S. PATENT DOCUMENTS

| | | | |
|---|---|---|---|
| 2005/0153411 A1* | 7/2005 | Wahlbom | C12N 1/18 435/161 |
| 2011/0027847 A1 | 2/2011 | Matsushika et al. | |
| 2011/0081698 A1 | 4/2011 | Noda et al. | |
| 2011/0137088 A1* | 6/2011 | Borden | C12P 7/065 568/840 |
| 2011/0165660 A1* | 7/2011 | Picataggio | C12N 9/88 435/254.21 |
| 2012/0093884 A1 | 4/2012 | Vesikari et al. | |
| 2013/0095538 A1 | 4/2013 | Katahira et al. | |
| 2014/0256011 A1 | 9/2014 | Zelle et al. | |
| 2016/0002674 A1 | 1/2016 | Onishi et al. | |

FOREIGN PATENT DOCUMENTS

| | | |
|---|---|---|
| JP | 2008-253153 A | 10/2008 |
| JP | 2009-195220 | 9/2009 |
| JP | 2010-45999 | 3/2010 |
| JP | 2010-239925 | 10/2010 |
| JP | 2011-24500 | 2/2011 |
| JP | 2011-147445 A | 8/2011 |
| JP | 2013-50000 A | 1/2013 |
| JP | 2013-540773 A | 11/2013 |
| WO | WO 03/078643 A1 | 9/2003 |
| WO | WO 2009/139349 | 11/2009 |
| WO | WO 2011/010923 A1 | 1/2011 |
| WO | WO 2011/078262 A1 | 6/2011 |
| WO | WO 2011/140386 A2 | 11/2011 |
| WO | WO 2012/058603 A1 | 5/2012 |
| WO | WO 2012/067510 A1 | 5/2012 |
| WO | WO 2013/061941 A1 | 5/2013 |

OTHER PUBLICATIONS

E. Bellissimi et al., "Effects of Acetic Acid on the Kinetics of Xylose Fermentation by an Engineered, Xylose-isomerase-based *Saccharomyces cerevisiae* Strain," FEMS Yeast Res., vol. 9, (2009), pp. 358-364.

S. Helle et al., "Effect of Inhibitory Compounds Found in Biomass Hydrolysates on Growth and Xylose Fermentation by a Genetically Engineered Strain of *S. cerevisiae*," Enzyme and Microbial Technology, vol. 33, (2003), pp. 786-792.

A. Gilbert et al., "Rapid Strain Improvement Through Optimized Evolution in the Cytostat," Biotechnology and Bioengineering, vol. 103, No. 3 (Jun. 15, 2009), pp. 500-512.

J. Zhang et al., "Improvement of Acetic Acid Tolerance and Fermentation Performance of *Saccharomyces cerevisiae* by Disruption of the FPS1 Aquaglyceroporin Gene," Biotechnol. Lett., vol. 33 (2011), pp. 277-284.

V. Medina et al., "Elimination of Glycerol Production in Anaerobic Cultures of a *Saccharomyces cerevisiae* Strain Engineered to Use Acetic Acid as an Electron Acceptor," Applied and Environmental Microbiology (Jan. 2010), pp. 190-195.

M. Sonderegger et al., "Metabolic Engineering of a Phosphoketolase Pathway for Pentose Catabolism in *Saccharomyces cerevisiae*," Applied and Environmental Microbiology (May 2004), pp. 2892-2897.

L. Zhang et al., "Improving the Ethanol Yield by Reducing Glycerol Formation Using Cofactor Regulation in *Saccharomyces cerevisiae*," Biotechnol. Lett., vol. 33 (2011), pp. 1375-1380.

U.S. Appl. No. 14/767,821, having national stage entry on Aug. 13, 2015 (available in PAIR).

Office Action issued in U.S. Appl. No. 14/767,821 dated Aug. 17. 2016,.

Office Action issued in U.S. Appl. No. 14/767,821 dated Oct. 27, 2016.

Johansson, Bjorn. et al. "The Non-Oxidative Pentose Phosphate Pathway Controls the Fermentation Rate of Xylulose but Not of Xylose in *Socobafornycaa Cerevisiae*", FEMS Yeast Research 2 (2002), pp. 277-282.

GenBank NCBI Reference Sequence XP_001703585.1, 'Dual Function Alcohol Dehydrogenase/Acetaldehyde Dehydrogenase [Chlarnydomortas Reinhardtii], May 2009, retrieved from https://www.ncbi.nlm.nih.gov/protein/XP_001703585.

Final Office Action issued in U.S. Appl. No. 14/767,821 dated Mar. 8, 2017.

Advisory Action issued in U.S. Appl. No. 14/767,821 dated Jul. 18, 2017.

MetaCyc Accession No. G-9110, obtained from http://akongo.psb.ugent.be/META/NEW-IMAGE?type=GENE&object=G-9110, last viewed on Jul. 12, 2017, 6 pages.

Office Action issued in U.S. Appl. No. 14/767,821 dated Sep. 15, 2017.

Gomes, L.H., "Increase on Ethanol Production by Blocking the $ADH_2$ Gene Expression in $GFP_3$ », Transformed Saccharomyces Cerevisiae," Greener Journal of Biological Sciences," vol. 3(1), pp. 058-060, Jan. 2013.

* cited by examiner

METHOD FOR PRODUCING ETHANOL USING RECOMBINANT YEAST

CROSS-REFERENCE TO RELATED APPLICATIONS

This application is a national phase application of International Application No. PCT/JP2012/077284, filed Oct. 23, 2012, and claims the priority of Japanese Application No. 2011-233300, filed Oct. 24, 2011, the content of both of which is incorporated herein by reference.

TECHNICAL FIELD

The present invention relates to a method for producing ethanol using a recombinant yeast strain having xylose-metabolizing ability.

BACKGROUND ART

A cellulosic biomass is an effective starting material for a useful alcohol, such as ethanol, or an organic acid. In order to increase the amount of ethanol produced with the use of a cellulosic biomass, yeast strains capable of utilizing a xylose, which is a pentose, as a substrate have been developed. For example, Patent Literature 1 discloses a recombinant yeast strain resulting from incorporation of a xylose reductase gene and a xylitol dehydrogenase gene derived from *Pichia stipitis* and a xylulokinase gene derived from *S. cerevisiae* into its chromosome.

It is known that a large amount of acetic acid is contained in a hydrolysate of a cellulosic biomass and that acetic acid inhibits ethanol fermentation by a yeast strain. In the case of a yeast strain into which a xylose-assimilating gene has been introduced, in particular, acetic acid is known to inhibit ethanol fermentation carried out with the use of xylose as a saccharide source at a significant level (Non-Patent Literature 1 and 2).

A mash (moromi) resulting from fermentation of a cellulosic biomass saccharified with a cellulase is mainly composed of unfermented residue, poorly fermentable residue, enzymes, and fermenting microorganisms. Use of a mash-containing reaction solution for the subsequent fermentation process enables the reuse of fermenting microorganisms, reduction of the quantity of fermenting microorganisms to be introduced, and cost reduction. In such a case, however, acetic acid contained in the mash is simultaneously introduced, the concentration of acetic acid contained in a fermentation medium is increased as a consequence, and this may inhibit ethanol fermentation. In the case of a continuous fermentation technique in which the mash in a fermentation tank is transferred to a flash tank in which a reduced pressure level is maintained, ethanol is removed from the flash tank, and the mash is returned to the fermentation tank, although removal of acetic acid from the mash is difficult. Thus, inhibition of acetic acid-mediated fermentation would be critical.

In order to avoid inhibition of fermentation by acetic acid, there are reports concerning ethanol fermentation ability in the presence of acetic acid that has been improved by means of LPP1 or ENA1 gene overexpression (Non-Patent Literature 3) or FPS1 gene disruption (Non-Patent Literature 4) of *Saccharomyces cerevisiae*, which is a strain generally used for ethanol fermentation. However, such literature reports the results concerning ethanol fermentation conducted with the use of a glucose substrate, and the effects on ethanol fermentation conducted with the use of a xylose substrate, which is inhibited by acetic acid at a significant level, remain unknown. Even if the mutant yeast strains reported in such literature were used, the amount of acetic acid carry-over, which would be problematic at the time of the reuse of fermenting microorganisms or continuous fermentation, would not be reduced.

Alternatively, inhibition of fermentation by acetic acid may be avoided by metabolization of acetic acid in a medium simultaneously with ethanol fermentation. However, acetic acid metabolism is an aerobic reaction, which overlaps the metabolic pathway of ethanol. While acetic acid metabolism may be achieved by conducting fermentation under aerobic conditions, accordingly, ethanol as a target substance would also be metabolized.

As a means for metabolizing acetic acid under anaerobic conditions in which ethanol is not metabolized, assimilation of acetic acid achieved by introduction of the mhpF gene encoding acetaldehyde dehydrogenase (EC 1.2.1.10) into a *Saccharomyces cerevisiae* strain in which the GPD1 and GPD2 genes of the pathway of glycerine production had been destroyed has been reported (Non-Patent Literature 5 and Patent Literature 2). Acetaldehyde dehydrogenase catalyzes the reversible reaction described below.

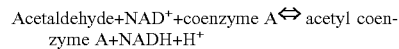

The pathway of glycerine production mediated by the GPD1 and GPD2 genes is a pathway that oxidizes excessive coenzyme NADH resulting from metabolism into $NAD^+$, as shown in the following chemical reaction.

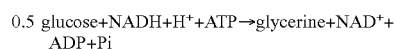

The reaction pathway is destructed by disrupting the GPD1 and GPD2 genes, excessive coenzyme NADH is supplied through introduction of mhpF, and the reaction proceeds as shown below.

Acetyl coenzyme A is synthesized from acetic acid by acetyl-CoA synthetase, and acetaldehyde is converted into ethanol. Eventually, excessive coenzyme NADH is oxidized and acetic acid is metabolized, as shown in the following chemical reaction.

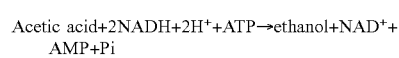

As described above, it is necessary to destroy the glycerine pathway in order to impart acetic acid metabolizing ability to a yeast strain. However, the GPD1- and GPD2-disrupted strain is known to have significantly lowered fermentation ability, and utility at the industrial level is low. Neither Non-Patent Literature 5 nor Patent Literature 2 concerns the xylose-assimilating yeast strain, and, accordingly, whether or not the strain of interest would be effective at the time of xylose assimilation is unknown.

A strain resulting from introduction of the mhpF gene into a strain that was not subjected to GPD1 or GPD2 gene disruption has also been reported (Non-Patent Literature 6). While Non-Patent Literature 6 reports that the amount of acetic acid production is reduced upon introduction of the mhpF gene, it does not report that acetic acid in the medium would be reduced. In addition, Non-Patent Literature 6 does not relate to a xylose-assimilating yeast strain.

Also, there are reports concerning the introduction of the acetaldehyde dehydrogenase gene (derived from *Entamoeba histolytica*) into a xylose-assimilating yeast strain into which the xylose reductase (XYL1) gene (derived from *Pichia stipitis*), the xylitol dehydrogenase (XYL2) gene (derived from *Pichia stipitis*), and the xylulokinase (XKS1) gene (derived from *Saccharomyces cerevisiae*) had been introduced (Non-Patent Literature 7 and Patent Literature 3). According to such literatures, however, acetic acid assimilation did not take place at the time of xylose assimilation, and no difference was observed between a strain into which the acetaldehyde dehydrogenase gene had been introduced and a strain into which the acetaldehyde dehydrogenase gene had not been introduced in terms of acetic acid concentration in the medium.

According to conventional techniques, as described above, acetic acid would not be efficiently metabolized or degraded under conditions in which ethanol fermentation and xylose assimilation take place simultaneously.

CITATION LIST

Patent Literature

{PTL 1}
JP 2009-195220 A
{PTL 2}
WO 2011/010923
{PTL 3}
WO 2003/078643

Non-Patent Literature

{NPL 1}
FEMS Yeast Research, vol. 9, 2009, pp. 358-364
{NPL 2}
Enzyme and Microbial Technology 33, 2003, pp. 786-792
{NPL 3}
Biotechnol. Bioeng., 2009, 103 (3): pp. 500-512
{NPL 4}
Biotechnol. Lett., 2011, 33: pp. 277-284
{NPL 5}
Appl. Environ. Microbiol., 2010, 76: pp. 190-195
{NPL 6}
Biotechnol. Lett., 2011, 33: pp. 1375-1380
{NPL 7}
Appl. Environ. Microbiol., 2004, 70: pp. 2892-2897

SUMMARY OF THE INVENTION

Technical Problem

Under the above circumstances, it is an object of the present invention to provide a method for producing ethanol using a recombinant yeast strain capable of metabolizing acetic acid in a medium to lower acetic acid concentration therein when, in particular, performing xylose assimilation and ethanol fermentation using a yeast strain having xylose-metabolizing ability.

Solution to Problem

The present inventors have conducted concentrated studies in order to attain the above object. As a result, they discovered that a recombinant yeast strain resulting from introduction of a particular acetaldehyde dehydrogenase gene into a yeast strain having xylose-metabolizing ability would enable metabolization of acetic acid in a medium when performing ethanol fermentation while performing cellulose saccharification in a medium containing cellulose and xylose. This has led to the completion of the present invention.

The present invention includes the following.

(1) A method for producing ethanol comprising a step of culturing a recombinant yeast strain having xylose-metabolizing ability and comprising an acetaldehyde dehydrogenase gene introduced thereinto in a medium containing cellulose, cellulase, and xylose to perform ethanol fermentation.

(2) The method for producing ethanol according to (1), wherein the yeast strain is a recombinant yeast strain comprising a xylose metabolism-associated gene introduced thereinto.

(3) The method for producing ethanol according to (1), wherein the acetaldehyde dehydrogenase gene encodes mhpF, which is acetaldehyde dehydrogenase derived from *E. coli*.

(4) The method for producing ethanol according to (3), wherein mhpF, which is acetaldehyde dehydrogenase derived from *E. coli*, is the protein (a) or (b) below:

(a) a protein comprising the amino acid sequence as shown in SEQ ID NO: 2; or
(b) a protein comprising an amino acid sequence having 70% or higher identity with the amino acid sequence as shown in SEQ ID NO: 2 and having acetaldehyde dehydrogenase activity.

(5) The method for producing ethanol according to (2), wherein the xylose metabolism-associated gene is the xylose reductase gene, the xylitol dehydrogenase gene, or the xylulokinase gene.

(6) The method for producing ethanol according to (1), wherein the ethanol fermentation proceeds simultaneously at least with the cellulose saccharification.

(7) The method for producing ethanol according to (1), wherein the recombinant yeast strain allows high-level expression of the alcohol dehydrogenase gene having activity of converting acetaldehyde into ethanol.

(8) The method for producing ethanol according to (1), wherein the recombinant yeast strain shows a lowered expression level of the alcohol dehydrogenase gene having activity of converting ethanol into acetaldehyde.

This description includes part or all of the content as disclosed in the description and/or drawings of Japanese Patent Application No. 2011-233300, which is a priority document of the present application.

Advantageous Effects of Invention

According to the method for producing ethanol of the present invention, acetic acid concentration in a medium can be lowered, and inhibition of fermentation caused by acetic acid can be effectively avoided. As a result, the method for producing ethanol of the present invention is capable of maintaining high efficiency for ethanol fermentation performed with the use of xylose as a saccharide source and achieving excellent ethanol yield. Accordingly, the method for producing ethanol of the present invention enables reduction of the amount of acetic acid carry-over at the time of, for example, the reuse of the recombinant yeast strain or use thereof for continuous culture, thereby allowing maintenance of an excellent ethanol yield.

DESCRIPTION OF EMBODIMENTS

Figure 1:
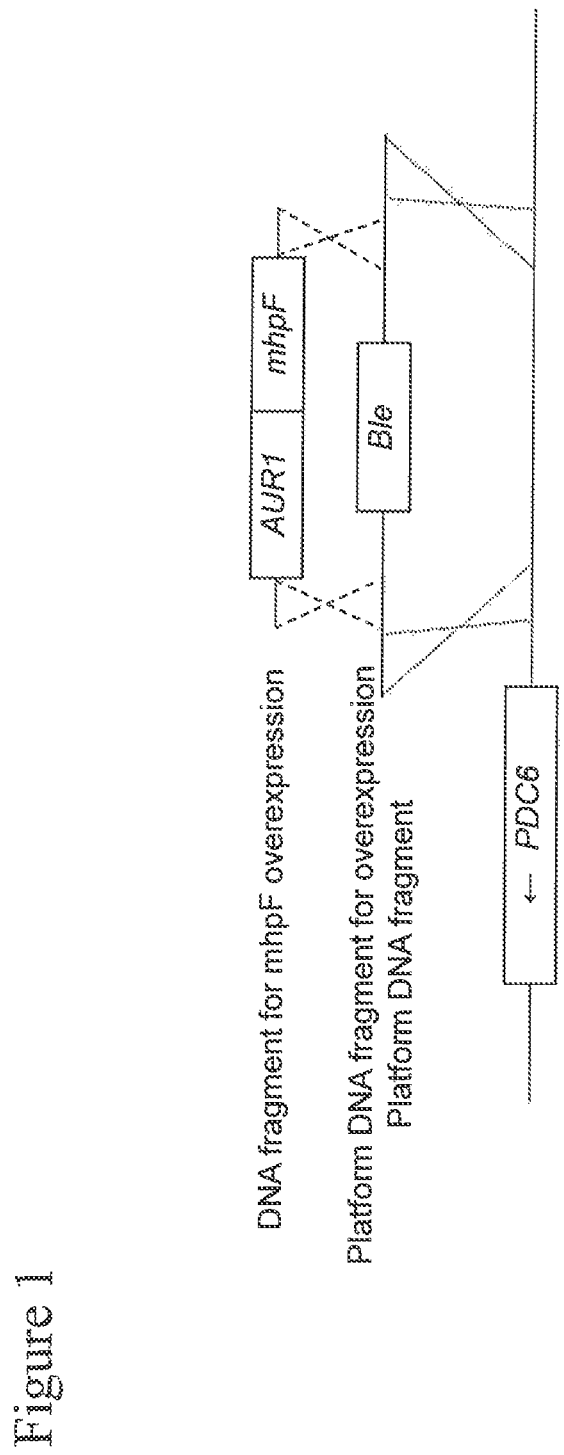
FIG. 1 is a schematic diagram illustrating a procedure for preparing a mhpF gene-overexpressing strain.

Hereafter, the present invention is described in greater detail with reference to the drawings and the examples.

The method for producing ethanol of the present invention is a method for synthesizing ethanol from a saccharide source contained in a medium with the use of a recombinant yeast strain having xylose-metabolizing ability into which an acetaldehyde dehydrogenase gene has been introduced. According to the method for producing ethanol of the present invention, the recombinant yeast strain can metabolize acetic acid contained in a medium, and acetic acid concentration in a medium is lowered in association with ethanol fermentation.

<Recombinant Yeast Strain>

A recombinant yeast strain used in the method for producing ethanol of the present invention has xylose-metabolizing ability and comprises at least an acetaldehyde dehydrogenase gene introduced thereinto. When a yeast strain has xylose-metabolizing ability, such ability may have been imparted as a result of introduction of a xylose isomerase gene into a yeast strain that does not inherently has xylose-metabolizing ability. Alternatively, a yeast strain has a xylose metabolism-associated gene and inherently has xylose-metabolizing ability. That is, the term "yeast strain having xylose-metabolizing ability" refers to a recombinant yeast strain resulting from introduction of a xylose metabolism-associated gene or a yeast strain that inherently has a xylose metabolism-associated gene.

A yeast strain having xylose-metabolizing ability is capable of assimilating xylose contained in a medium to produce ethanol. Xylose contained in a medium may be obtained by saccharification of xylan or hemicellulose comprising xylose as a constituent sugar. Alternatively, it may be a substance supplied to a medium as a result of saccharification of xylan or hemicellulose contained in a medium by a carbohydrase. The latter case refers to the so-called simultaneous saccharification and fermentation system.

Examples of xylose metabolism-associated genes include a xylose reductase gene encoding a xylose reductase that converts xylose into xylitol, a xylitol dehydrogenase gene encoding a xylitol dehydrogenase that converts xylitol into xylulose, and a xylulokinase gene encoding a xylulokinase that phosphorylates xylulose to produce xylulose 5-phosphate. Xylulose 5-phosphate produced by a xylulokinase will be metabolized in a pentose phosphate pathway.

Examples of xylose metabolism-associated genes include, but are not particularly limited to, a xylose reductase gene and a xylitol dehydrogenase gene derived from *Pichia stipitis* and a xylulokinase gene derived from *Saccharomyces cerevisiae* (see Eliasson A. et al., Appl. Environ. Microbiol., 66: 3381-3386; and Toivari M. N. et al., Metab. Eng., 3: 236-249). In addition, xylose reductase genes derived from *Candida tropicalis* and *Candida prapsilosis*, xylitol dehydrogenase genes derived from *Candida tropicalis* and *Candida prapsilosis*, and a xylulokinase gene derived from *Pichia stipitis* can be used. Examples of the xylose isomerase genes that can be used include a gene derived from the anaerobic fungus *Piromyces* sp. strain E2 (JP 2005-514951 A), a gene derived from the anaerobic fungus *Cyllamyces aberensis*, a gene derived from a bacterial strain (i.e., *Bacteroides thetaiotaomicron*), a gene derived from a bacterial strain (i.e., *Clostridium phytofermentans*), and a gene derived from a strain of the *Streptomyces murinus* cluster.

Examples of yeast strains that inherently have xylose-metabolizing ability include, but are not particularly limited to, *Pichia stipitis, Candida tropicalis*, and *Candida prapsilosis*.

An acetaldehyde dehydrogenase gene to be introduced into a yeast strain having xylose-metabolizing ability is not particularly limited, and a gene derived from any species of organism may be used. When acetaldehyde dehydrogenase genes derived from organisms other than a fungus such as yeast (e.g., genes derived from bacteria, animals, plants, insects, or algae) are used, it is preferable that the nucleotide sequence of the gene be modified in accordance with the frequency of codon usage in a yeast strain into which the gene of interest is to be introduced.

More specifically, the mhpF gene of *E. coli* and the ALDH1 gene of *Entamoeba histolytica* as disclosed in Applied and Environmental Microbiology, May 2004, pp. 2892-2897, Vol. 70, No. 5 can be used as the acetaldehyde dehydrogenase genes. The nucleotide sequence of the mhpF gene of *E. coli* and the amino acid sequence of a protein encoded by the mhpF gene are shown in SEQ ID NOs: 1 and 2, respectively.

The acetaldehyde dehydrogenase genes are not limited to the genes identified by SEQ ID NOs: 1 and 2. It may be a paralogous gene or a homologous gene in the narrow sense having different nucleotide and amino acid sequences.

The acetaldehyde dehydrogenase genes are not limited to the genes identified by SEQ ID NOs: 1 and 2. For example, it may be a gene comprising an amino acid sequence having 70% or higher, preferably 80% or higher, more preferably 90% or higher, and most preferably 95% or higher sequence similarity to or identity with the amino acid sequence as shown in SEQ ID NO: 2 and encoding a protein having acetaldehyde dehydrogenase activity. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of the aforementioned amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such completely identical amino acid residues.

Further, the acetaldehyde dehydrogenase genes are not limited to the genes identified by SEQ ID NOs: 1 and 2. For example, it may be a gene comprising an amino acid sequence derived from the amino acid sequence as shown in SEQ ID NO: 2 by substitution, deletion, insertion, or addition of one or several amino acids and encoding a protein having acetaldehyde dehydrogenase activity. The term "several" used herein refers to, for example, 2 to 30, preferably 2 to 20, more preferably 2 to 10, and most preferably 2 to 5.

Furthermore, the acetaldehyde dehydrogenase genes are not limited to the genes identified by SEQ ID NOs: 1 and 2.

For example, it may be a gene hybridizing under stringent conditions to the full-length sequence or a partial sequence of a complementary strand of DNA comprising the nucleotide sequence as shown in SEQ ID NO: 1 and encoding a protein having acetaldehyde dehydrogenase activity. Under "stringent conditions," so-called specific hybrids are formed, but non-specific hybrids are not formed. Such conditions can be adequately determined with reference to, for example, Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42 degrees C. to 68 degrees C. and preferably 42 degrees C. to 65 degrees C., for example. Further specifically, the sodium concentration is 5×SSC (83 mM NaCl, 83 mM sodium citrate), and the temperature is 42 degrees C.

As described above, whether or not a gene comprising a nucleotide sequence that differs from the sequence shown in SEQ ID NO: 1 or a gene encoding an amino acid sequence that differs from the sequence shown in SEQ ID NO: 2 would function as an acetaldehyde dehydrogenase gene may be determined by, for example, preparing an expression vector comprising the gene of interest incorporated into an adequate site between a promoter and a terminator, transforming an *E. coli* host using such expression vector, and assaying acetaldehyde dehydrogenase activity of the protein expressed. Acetaldehyde dehydrogenase activity can be assayed by preparing a solution containing acetaldehyde, CoA, and $NAD^+$ as substrates, allowing the target protein to react at adequate temperature, and converting the generated acetyl phosphate into acetyl phosphate with the aid of a phosphate acetyl transferase or spectroscopically assaying the generated NADH.

A recombinant yeast strain used in the method for producing ethanol of the present invention has xylose-metabolizing ability and comprises at least the acetaldehyde dehydrogenase gene introduced thereinto. A recombinant yeast strain may further comprise other gene(s) introduced thereinto, and such other gene(s) are not particularly limited. For example, a gene involved in the sugar metabolism of glucose may be introduced into such recombinant yeast strain. For example, a recombinant yeast strain can have beta-glucosidase activity resulting from the introduction of the beta-glucosidase gene.

The term "beta-glucosidase activity" used herein refers to the activity of catalyzing a hydrolysis reaction of a beta-glycoside bond of a sugar. Specifically, beta-glucosidase is capable of degrading a cellooligosaccharide, such as cellobiose, into glucose. The beta-glucosidase gene can be introduced in the form of a cell-surface display gene. The term "cell-surface display gene" used herein refers to a gene that is modified to display a protein to be encoded by the gene on a cell surface. For example, a cell-surface display beta-glucosidase gene is a gene resulting from fusion of a beta-glucosidase gene with a cell-surface localized protein gene. A cell-surface localized protein is fixed and present on a yeast cell surface layer. Examples include agglutinative proteins, such as alpha- or a-agglutinin and FLO proteins. In general, a cell-surface localized protein comprises an N-terminal secretory signal sequence and a C-terminal GPI anchor attachment recognition signal sequence. While a cell-surface localized protein shares properties with a secretory protein in terms of the presence of a secretory signal, these proteins differ from each other in that the cell-surface localized protein is transported while fixed to a cell membrane through a GPI anchor. When a cell-surface localized protein passes through a cell membrane, a GPI anchor attachment recognition signal sequence is selectively cut, it binds to a GPI anchor at a newly protruded C-terminal region, and it is then fixed to the cell membrane. Thereafter, the root of the GPI anchor is cut by phosphatidylinositol-dependent phospholipase C (PI-PLC). Subsequently, a protein separated from the cell membrane is integrated into a cell wall, fixed onto a cell surface layer, and then localized on a cell surface layer (see, for example, JP 2006-174767 A).

The beta-glucosidase gene is not particularly limited, and an example is a beta-glucosidase gene derived from *Aspergillus aculeatus* (Murai, et al., Appl. Environ. Microbiol., 64: 4857-4861). In addition, a beta-glucosidase gene derived from *Aspergillus oryzae*, a beta-glucosidase gene derived from *Clostridium cellulovorans*, and a beta-glucosidase gene derived from *Saccharomycopsis fibligera* can be used.

In addition to or other than the beta-glucosidase gene, a gene encoding another cellulase-constituting enzyme may have been introduced into a recombinant yeast strain used in the method for producing ethanol of the present invention. Examples of cellulase-constituting enzymes other than beta-glucosidase include exo-cellobiohydrolases that liberate cellobiose from the terminus of crystalline cellulose (CBH1 and CBH2) and endo-glucanase (EG) that cannot degrade crystalline cellulose but cleaves a non-crystalline cellulose (amorphous cellulose) chain at random.

Examples of other genes to be introduced into a recombinant yeast strain include an alcohol dehydrogenase gene (the ADH1 gene) having activity of converting acetaldehyde into ethanol, an acetyl-CoA synthetase gene (the ACS1 gene) having activity of converting acetic acid into acetyl-CoA, and genes having activity of converting acetaldehyde into acetic acid (i.e., the ALD4, ALD5, and ALD6 genes). The alcohol dehydrogenase gene (the ADH2 gene) having activity of converting ethanol into acetaldehyde may be disrupted.

In addition, it is preferable that a recombinant yeast strain used in the method for producing ethanol of the present invention allow high-level expression of the alcohol dehydrogenase gene (the ADH1 gene) having activity of converting acetaldehyde into ethanol. In order to realize high-level expression of such gene, for example, a promoter of the inherent gene may be replaced with a promoter intended for high-level expression, or an expression vector enabling expression of such gene may be introduced into a yeast strain.

The nucleotide sequence of the ADH1 gene of *Saccharomyces cerevisiae* and the amino acid sequence of a protein encoded by such gene are shown in SEQ ID NOs: 70 and 71, respectively. The alcohol dehydrogenase gene to be expressed at high level is not limited to the genes identified by SEQ ID NOs: 70 and 71. It may be a paralogous gene or a homologous gene in the narrow sense having different nucleotide and amino acid sequences.

The alcohol dehydrogenase genes are not limited to the genes identified by SEQ ID NOs: 70 and 71. For example, it may be a gene comprising an amino acid sequence having 70% or higher, preferably 80% or higher, more preferably 90% or higher, and most preferably 95% or higher sequence similarity to or identity with the amino acid sequence as shown in SEQ ID NO: 71 and encoding a protein having alcohol dehydrogenase activity. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of the aforementioned amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such completely identical amino acid residues.

Furthermore, the alcohol dehydrogenase genes are not limited to the genes identified by SEQ ID NOs: 70 and 71. For example, it may be a gene comprising an amino acid sequence derived from the amino acid sequence as shown in SEQ ID NO: 71 by substitution, deletion, insertion, or addition of one or several amino acids and encoding a protein having acetaldehyde dehydrogenase activity. The term "several" used herein refers to, for example, 2 to 30, preferably 2 to 20, more preferably 2 to 10, and most preferably 2 to 5.

Furthermore, the alcohol dehydrogenase genes are not limited to the genes identified by SEQ ID NOs: 70 and 71. For example, it may be a gene hybridizing under stringent conditions to the full-length sequence or a partial sequence of a complementary strand of DNA comprising the nucleotide sequence as shown in SEQ ID NO: 70 and encoding a protein having acetaldehyde dehydrogenase activity. Under "stringent conditions," so-called specific hybrids are formed, but non-specific hybrids are not formed. Such conditions can be adequately determined with reference to, for example, Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42 degrees C. to 68 degrees C. and preferably 42 degrees C. to 65 degrees C., for example. Further specifically, the sodium concentration is 5×SSC (83 mM NaCl, 83 mM sodium citrate), and the temperature is 42 degrees C.

As described above, whether or not a gene comprising a nucleotide sequence that differs from the sequence shown in SEQ ID NO: 70 or a gene encoding an amino acid sequence that differs from the sequence shown in SEQ ID NO: 71 would function as an alcohol dehydrogenase gene may be determined by, for example, preparing an expression vector comprising the gene of interest incorporated into an adequate site between a promoter and a terminator, transforming a yeast host using such expression vector, and assaying alcohol dehydrogenase activity of the protein expressed. Alcohol dehydrogenase activity can be assayed by preparing a solution containing alcohol and NAD+ or NADP+ as substrates, allowing the target protein to react at adequate temperature, and assaying the generated aldehyde or spectroscopically assaying NADH or NADPH.

A recombinant yeast strain used in the method for producing ethanol of the present invention is preferably characterized by a lowered expression level of the alcohol dehydrogenase gene (the ADH2 gene) having activity of converting ethanol into aldehyde. In order to lower the expression level of such gene, a promoter of the inherent gene of interest may be modified, or such gene may be disrupted. Examples of techniques for suppressing gene expression include the transposon technique, the transgene technique, post-transcriptional gene silencing, the RNAi technique, the nonsense mediated decay (NMD) technique, the ribozyme technique, the anti-sense technique, the miRNA (micro-RNA) technique, and the siRNA (small interfering RNA) technique.

The nucleotide sequence of the ADH2 gene of *Saccharomyces cerevisiae* and the amino acid sequence of a protein encoded by such gene are shown in SEQ ID NOs: 72 and 73, respectively. The target alcohol dehydrogenase genes are not limited to the genes identified by SEQ ID NOs: 72 and 73. It may be a paralogous gene or a homologous gene in the narrow sense having different nucleotide and amino acid sequences.

The alcohol dehydrogenase genes are not limited to the genes identified by SEQ ID NOs: 72 and 73. For example, it may be a gene comprising an amino acid sequence having 70% or higher, preferably 80% or higher, more preferably 90% or higher, and most preferably 95% or higher sequence similarity to or identity with the amino acid sequence as shown in SEQ ID NO: 73 and encoding a protein having alcohol dehydrogenase activity. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the alcohol dehydrogenase genes are not limited to the genes identified by SEQ ID NOs: 72 and 73. For example, it may be a gene comprising an amino acid sequence derived from the amino acid sequence as shown in SEQ ID NO: 73 by substitution, deletion, insertion, or addition of one or several amino acids and encoding a protein having acetaldehyde dehydrogenase activity. The term "several" used herein refers to, for example, 2 to 30, preferably 2 to 20, more preferably 2 to 10, and most preferably 2 to 5.

Furthermore, the alcohol dehydrogenase genes are not limited to the genes identified by SEQ ID NOs: 72 and 73. For example, it may be a gene hybridizing under stringent conditions to the full-length sequence or a partial sequence of a complementary strand of DNA comprising the nucleotide sequence as shown in SEQ ID NO: 72 and encoding a protein having acetaldehyde dehydrogenase activity. Under "stringent conditions," so-called specific hybrids are formed, but non-specific hybrids are not formed. Such conditions can be adequately determined with reference to, for example, Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42 degrees C. to 68 degrees C. and preferably 42 degrees C. to 65 degrees C., for example. Further specifically, the sodium concentration is 5×SSC (83 mM NaCl, 83 mM sodium citrate), and the temperature is 42 degrees C. As described above, whether or not a gene comprising a nucleotide sequence that differs from the sequence shown in SEQ ID NO: 72 or a gene encoding an amino acid sequence that differs from the sequence shown in SEQ ID NO: 73 would function as an alcohol dehydrogenase gene may be determined by, for example, preparing an expression vector comprising the gene of interest incorporated into an adequate site between a promoter and a terminator, transforming a yeast host using such expression vector, and assaying alcohol dehydrogenase activity of the protein expressed. Alcohol dehydrogenase activity can be assayed by preparing a solution containing aldehyde and NADH or NADPH as substrates, allowing the target protein to react at adequate temperature, and assaying the generated alcohol or spectroscopically assaying NADP+. Further examples of other genes that can be introduced into a recombinant yeast strain include genes associated with the metabolic pathway of L-arabinose, which is a pentose contained in hemicellulose constituting a biomass. Examples of such genes include an L-arabinose isomerase gene, an L-ribulokinase gene, and an L-ribulose-5-phosphate-4-epimerase gene derived from prokaryotes and an L-arabitol-4-dehydrogenase gene and an L-xylose reductase gene derived from eukaryotes.

<Production of Recombinant Yeast Strain>

The acetaldehyde dehydrogenase gene is introduced into a host yeast genome, and a recombinant yeast strain that can be used in the present invention can be produced. The acetaldehyde dehydrogenase gene may be introduced into a recombinant yeast strain resulting from introduction of a xylose metabolism-associated gene into a yeast strain that does not have xylose-metabolizing ability, a yeast strain that inherently has xylose-metabolizing ability, or a yeast strain that does not have xylose-metabolizing ability together with the xylose metabolism-associated gene. Alternatively, the acetaldehyde dehydrogenase gene may be introduced into a yeast strain that does not have xylose-metabolizing ability, a yeast strain that inherently has xylose-metabolizing ability to prepare a recombinant yeast strain, and the xylose metabolism-associated gene may then be introduced into the recombinant yeast strain to impart the strain with xylose-metabolizing ability.

Examples of host yeast strains that can be used include, but are not particularly limited to, *Candida Shehatae*, *Pichia stipitis*, *Pachysolen tannophilus*, *Saccharomyces cerevisiae*, and *Schizosaccaromyces pombe*, with *Saccharomyces cerevisiae* being particularly preferable. Experimental yeast strains may also be used from the viewpoint of experimental convenience, or industrial (practical) strains may also be used from the viewpoint of practical usefulness. Examples of industrial strains include yeast strains used for the production of wine, sake, and shochu.

Use of a host yeast strain having homothallic properties is preferable. According to the technique disclosed in JP 2009-34036 A, multiple copies of genes can be easily introduced into a genome with the use of a yeast strain having homothallic properties. The term "yeast strain having homothallic properties" has the same meaning as the term "homothallic yeast strain." Yeast strains having homothallic properties are not particularly limited, and any yeast strains can be used. An example of a yeast strain having homothallic properties is, but is not limited to, the *Saccharomyces cerevisiae* OC-2 train (NBRC2260). Examples of other yeast strains having homothallic properties include an alcohol-producing yeast (Taiken No. 396, NBRC0216) (reference: "*Alcohol kobo no shotokusei*" ("Various properties of alcohol-producing yeast"), Shuken Kaiho, No. 37, pp. 18-22, 1998.8), an ethanol-producing yeast isolated in Brazil and in Japan (reference: "*Brazil to Okinawa de bunri shita Saccharomyces cerevisiae yaseikabu no idengakuteki seishitsu*" ("Genetic properties of wild-type *Saccharomyces cerevisiae* isolated in Brazil and in Okinawa"), the Journal of the Japan Society for Bioscience, Biotechnology, and Agrochemistry, Vol. 65, No. 4, pp. 759-762, 1991.4), and 180 (reference: "*Alcohol Hakkoryoku no tsuyoi kobo no screening*" ("Screening of yeast having potent alcohol-fermenting ability"), the Journal of the Brewing Society of Japan, Vol. 82, No. 6, pp. 439-443, 1987.6). In addition, the HO gene may be introduced into a yeast strain exhibiting heterothallic phenotypes in an expressible manner, and the resulting strain can be used as a yeast strain having homothallic properties. That is, the term "yeast strain having homothallic properties" used herein also refers to a yeast strain into which the HO gene has been introduced in an expressible manner.

The *Saccharomyces cerevisiae* OC-2 strain is particularly preferable since it has heretofore been used for wine brewing, and the safety thereof has been verified. As described in the examples below, the *Saccharomyces cerevisiae* OC-2 strain is preferable in terms of its excellent promoter activity at high sugar concentrations. In particular, the *Saccharomyces cerevisiae* OC-2 strain is preferable in terms of its excellent promoter activity for the pyruvate decarboxylase gene (PDC1) at high sugar concentrations.

Promoters of genes to be introduced are not particularly limited. For example, promoters of the glyceraldehyde-3-phosphate dehydrogenase gene (TDH3), the 3-phosphoglycerate kinase gene (PGK1), and the high-osmotic pressure response 7 gene (HOR7) can be used. The promoter of the pyruvate decarboxylase gene (PDC1) is particularly preferable in terms of its high capacity for expressing target genes in a downstream region at high levels.

Specifically, such gene may be introduced into the yeast genome together with an expression-regulating promoter or another expression-regulated region. Such gene may be introduced into a host yeast genome in such a manner that expression thereof is regulated by a promoter or another expression-regulated region of a gene that is inherently present therein.

The gene can be introduced into the genome by any conventional technique known as a yeast transformation technique. Specific examples include, but are not limited to, electroporation (Meth. Enzym., 194, p. 182, 1990), the spheroplast technique (Proc. Natl. Acad. Sci., U.S.A., 75, p. 1929, 1978), and the lithium acetate method (J. Bacteriology, 153, p. 163, 1983; Proc. Natl. Acad. Sci., U.S.A., 75, p. 1929, 1978; Methods in yeast genetics, 2000 Edition: A Cold Spring Harbor Laboratory Course Manual).

<Production of Ethanol>

When producing ethanol with the use of the recombinant yeast strain described above, ethanol fermentation is carried out by culture in a medium containing cellulose, cellulase, and xylose. A medium in which ethanol fermentation is carried out contains at least xylose and glucose generated by the action of cellulase imposed upon cellulose as carbon sources. The medium may contain another carbon source in advance.

Either or both of cellulose and xylose that are contained in a medium to be used for ethanol fermentation can be derived from a biomass. In other words, a medium to be used for ethanol fermentation may comprise a cellulosic biomass, cellulase that is capable of saccharification of cellulase contained in a cellulosic biomass, and hemicellulase that generates xylose through saccharification of hemicellulose contained in the cellulosic biomass. The cellulosic biomass may have been subjected to a conventional pretreatment technique. Examples of pretreatment techniques include, but are not particularly limited to, degradation of a lignin with a microorganism and grinding of a cellulosic biomass. For example, a ground cellulosic biomass may be subjected to pretreatment, such as soaking thereof in a dilute sulfuric acid solution, alkaline solution, or ionic solution, hydrothermal treatment, or fine grinding. Thus, the efficiency of biomass saccharification can be improved.

A saccharified solution resulting from saccharification of a cellulosic biomass may be added to the medium used for ethanol fermentation. In such a case, the saccharified solution contains remaining cellulose or cellulase and xylose derived from hemicellulose contained in a cellulosic biomass.

As described above, the method for producing ethanol of the present invention may employ the so-called simultaneous saccharification and fermentation process, in which the step of saccharification of cellulose contained in a medium with a cellulase proceeds concurrently with the process of ethanol fermentation carried out with the use of saccharide sources (i.e., xylose and glucose generated by saccharification). With the simultaneous saccharification and fermentation process, the step of saccharification of a cellulosic biomass is carried out simultaneously with the process of ethanol fermentation.

The recombinant yeast strain is capable of assimilating xylose contained in any medium and generating ethanol. Methods of saccharification are not particularly limited, and, for example, an enzymatic method involving the use of a cellulase preparation, such as cellulase or hemicellulase, may be employed. A cellulase preparation contains a plurality of enzymes involved in degradation of a cellulose chain and a hemicellulose chain, and it exhibits a plurality of types of activity, such as endoglucanase activity, endoxylanase activity, cellobiohydrolase activity, glucosidase activity, and xylosidase activity. Cellulase preparations are not particularly limited, and examples include cellulases produced by *Trichoderma reesei* and *Acremonium cellulolyticus*. Commercially available cellulase preparations may also be used.

In the simultaneous saccharification and fermentation process, a cellulase preparation and the recombinant microorganism are added to a medium containing a cellulosic biomass (a biomass after pretreatment may be used), and the recombinant yeast strain is cultured at a given temperature. Culture may be carried out at any temperature without particular limitation, and the temperature may be 25 degrees C. to 45 degrees C., and preferably 30 degrees C. to 40 degrees C. from the viewpoint of ethanol fermentation efficiency. The pH level of the culture solution is preferably 4 to 6. When conducting culture, stirring or shaking may be carried out. Alternatively, the simultaneous saccharification and fermentation process may be carried out irregularly in such a manner that saccharification is first carried out at an optimal temperature for an enzyme (40 degrees C. to 70 degrees C.), temperature is lowered to a given level (30 degrees C. to 40 degrees C.), and a yeast strain is then added thereto.

According to the method for producing ethanol with the use of the recombinant yeast strain of the present invention, ethanol fermentation is followed by recovery of ethanol from the medium. Ethanol may be recovered by any conventional means without particular limitation. After the completion of the process of ethanol fermentation mentioned above, for example, a liquid layer containing ethanol is separated from a solid layer containing the recombinant yeast strain or solid matter via solid-solution separation. Thereafter, ethanol contained in a liquid layer is separated and purified by distillation, so that highly purified ethanol can be recovered. The degree of ethanol purification can be adequately determined in accordance with the purpose of use of the ethanol.

When producing ethanol with the use of a saccharide derived from a biomass, in general, a fermentation inhibitor, such as acetic acid or furfural, may occasionally be generated in the process of pretreatment or saccharification. In particular, acetic acid is known to inhibit the growth and multiplication of yeast strains and to lower the efficiency for ethanol fermentation conducted with the use of xylose as a saccharide source.

According to the present invention, however, recombinant yeast strains into which the acetaldehyde dehydrogenase gene has been introduced are used. Thus, acetic acid contained in a medium can be metabolized, and acetic acid concentration in a medium can be maintained at a low level. Accordingly, the method for producing ethanol of the present invention can achieve an ethanol yield superior to that achieved with the use of yeast strains into which the acetaldehyde dehydrogenase gene has not been introduced.

According to the method for producing ethanol of the present invention, acetic acid concentration in a medium remains low after the recombinant yeast strain has been cultured for a given period of time. Even if part of the medium after such given period of time is used for a continuous culture system in which a new culture process is initiated, accordingly, the amount of acetic acid carry-over can be reduced. According to the method for producing ethanol of the present invention, therefore, the amount of acetic acid carry-over can be reduced even when cells are recovered and reused after the completion of the process of ethanol fermentation.

EXAMPLES

Hereafter, the present invention is described in greater detail with reference to the examples, although the technical scope of the present invention is not limited to these examples.

Example 1

In Example 1, a recombinant yeast strain was prepared through introduction of an acetaldehyde dehydrogenase gene derived from *E. coli* (the mhpF gene) into a xylose-assimilating yeast strain, and acetic acid metabolizing ability of the recombinant yeast strain was evaluated.

<Construction of DNA Fragment for Overexpression of mhpF Gene>

With the use of the plasmid prepared in Reference Example 1 described in detail below, pCR-T_HIS3-P_TDH3-AUR1-C-P_TDH2-IDP2m-T_IDP2-PDC1part, as a template, a DNA fragment excluding the promoter region of the TDH2 gene and the IDP2 gene was amplified by PCR. A pair of PCR primers TB2158 (5'-ACCCGTGGCTGC-GAGCGACCAGCTAACTTGGTCGAC-3': SEQ ID NO:

3) and TB2797 (5'-CCTCATTGCTGGATAGAGCCT-CATCG-3': SEQ ID NO: 4) was used.

Separately, a DNA fragment containing a terminator region of the ERO1 gene and a DNA fragment containing a promoter region of the HOR7 gene were amplified using the genome of the OC2 yeast strain (NBRC2260) as a template. These primers used for PCR were designed with reference to the DNA sequence data stored in the *Saccharomyces* Genome Database (http://www.yeastgenome.org/), in such a manner that the amplified DNA fragments would overlap each other by about 15 bp. PCR for amplification of the DNA fragment containing a terminator region of the ERO1 gene was carried out using, as primers, TB2796 (5'-TC-TATCCAGCAATGAGGAGTGATTTTACAC-3': SEQ ID NO: 5) and TB2462 (5'-GAGCAACACAGTTTATCT-TATATGTATTCAATG-3': SEQ ID NO: 6). PCR for amplification of the DNA fragment containing a promoter region of the HOR7 gene was carried out using, as primers, TB2168 (5'-TTTTATTATTAGTCTTTTTTTTTTTT-GACAATATCTG-3': SEQ ID NO: 7) and 1132654 (5'-TCGCTCGCAGCCACGGGT-3': SEQ ID NO: 8).

The mhpF gene was amplified by PCR using, as a template, a sequence fully synthesized from a sequence in which codons had been transformed in accordance with the codon usage frequency of the yeast strain (purchased from GenScript). A pair of PCR primers TB2463 (5'-TAAACT-GTGTTGCTCTTATGCGGCCTCTCCTGC-3': SEQ ID NO: 9) and TB2464 (5'-AGACTAATAATAATAAATGT-CAAAGAGAAAAGTTGCTATATCG-3': SEQ ID NO: 10) was used. The DNA fragments were cloned into a plasmid using the In-Fusion™ Advantage PCR Cloning Kit (Clontech). The resulting plasmid was designated as pCR-T_HIS3-P_TDH3-AUR1-C-ERO1_T-mhpF-HOR7_P-PDC1 part.

<Preparation of Strain Overexpressing XYL1, XYL2, and XKS1 Genes and Homozygously Disrupting GRE3 Gene>

XYL1, XYL2, and XKS1 gene overexpression and GRE3 gene were heterozygously introduced into the homothallic diploid yeast strain; i.e., the *Saccharomyces cerevisiae* OC2-T strain (Saitoh, S. et al., J. Ferment. Bioeng., 1996, Vol. 81, pp. 98-104) (see Reference Example 2 below), and the resulting strain was allowed to sporulate in a sporulation medium (1% potassium phosphate, 0.1% yeast extract, 0.05% glucose, and 2% agar), so as to cause diploidization with the utilization of homothallic properties. A strain in which GRE3 genes are disrupted by integration of the XYL1, XYL2, and XKS1 genes into the GRE3 genetic loci of its chromosome was obtained. The resultant was designated as the Uz326 strain.

<Preparation of Strain Overexpressing mhpF Gene (FIG. 1)>

In order to introduce a DNA fragment for overexpression of the mhpF gene into the genome of the Uz326 strain, it is necessary that sequences of the homologous recombination regions; i.e. 5'- and 3'-terminal sequences, of the DNA fragment be located at positions in the vicinity of relevant chromosomes. Thus, the plasmid (pCR-5U_PDC6-T_HIS3-P_TDH3-Ble-T_URA3-PDC1part-5U_PDC6; see Reference Example 1 below) containing a DNA fragment (a platform DNA fragment for overexpression) for introduction of a sequence, which is composed of a DNA fragment comprising a terminator region of the HIS3 gene at the 5' terminus of the DNA fragment for overexpression of the mhpF gene and a promoter region of the TDH3 gene and a DNA fragment comprising a part of the PDC1 gene at the 5' terminus, into a site located upstream of the PDC6 gene was used as a template, so as to amplify a DNA fragment excluding the pCR-Blunt II TOPO vector portion by PCR. A pair of PCR primers TB0948 (5'-GTTGAAGTCGCCTGG-TAGCC-3': SEQ ID NO: 11) and TB0735 (5'-CGGTGATC-CCCTTGAAAAAG-3': SEQ ID NO: 12) was used. With the use of the Frozen-EZ Yeast Transformation II Kit (ZYMO RESEARCH), the amplified DNA fragment was transformed into the Uz326 strain in accordance with the protocols included in the kit. Thereafter, the resultant was seeded on a YPD plate containing zeocin (300 microgram/ml), culture was conducted at 30 degrees C. for 5 days, and the resulting transformant was designated as the Uz327 strain.

Subsequently, a DNA fragment excluding the pCR-Blunt II TOPO vector portion was amplified by PCR using pCR-T_HIS3-P_TDH3-AUR1-C-ERO1_T-mhpF-HOR7_P-PDC1part obtained above as a template. A pair of PCR primers TB1932 (5'-TCCCTCCACCAAAGGTGTTC-3': SEQ ID NO: 13) and TB0115 (5'-TTGCAAAGAACCGT-CACCAATG-3': SEQ ID NO: 14) was used. The amplified DNA fragment was transformed into the Uz327 strain using the Frozen-EZ Yeast Transformation II kit, and the resulting transformant was designated as the Uz370 strain.

<Fermentation Test>

The Uz370 strain and the Uz327 strain obtained in the manner described above were inoculated into YPD medium (10 g/l yeast extract, 20 g/l peptone, and 20 g/l, glucose), and culture was conducted at 150 rpm/min (shake width: 35 mm) and 30 degrees C. for 24 hours. A CX medium (100 g/l cellulose, 70 g/l xylose, 10 g/l yeast extract, 2.75 g/l acetic acid, and 40 FPU/g of cellulose (Cellic CTec2, a cellulase manufactured by Novozymes); adjusted to pH 6.0), a DX medium (100 g/l glucose, 70 g/l xylose, 10 g/l yeast extract, and 2.75 g/l acetic acid; adjusted to pH 6.0), an X medium (70 g/l xylose, 10 g/l yeast extract, and 2.75 g/l acetic acid; adjusted to pH 6.0) (28 ml each) and 10-mm nylon-coated iron balls were introduced into a 30-ml flask, the cultured strains were inoculated therein to adjust the optical density (OD) to 7.3, fermentation was carried out at 80 rpm/min (shake width: 35 mm) and 32 degrees C., and the amount of ethanol produced and the amount of acetic acid consumed were examined. Concentrations of ethanol and acetic acid were measured by HPLC (LC-10A, Shimadzu Seisakusho; column: AminexHPX-87H (BioRad); mobile phase: $0.01 NH_2SO_4$; flow rate: 0.6 ml/min; temperature: 30 degrees C.; detector: differential refractometer (RID-10A)).

Figure 2:
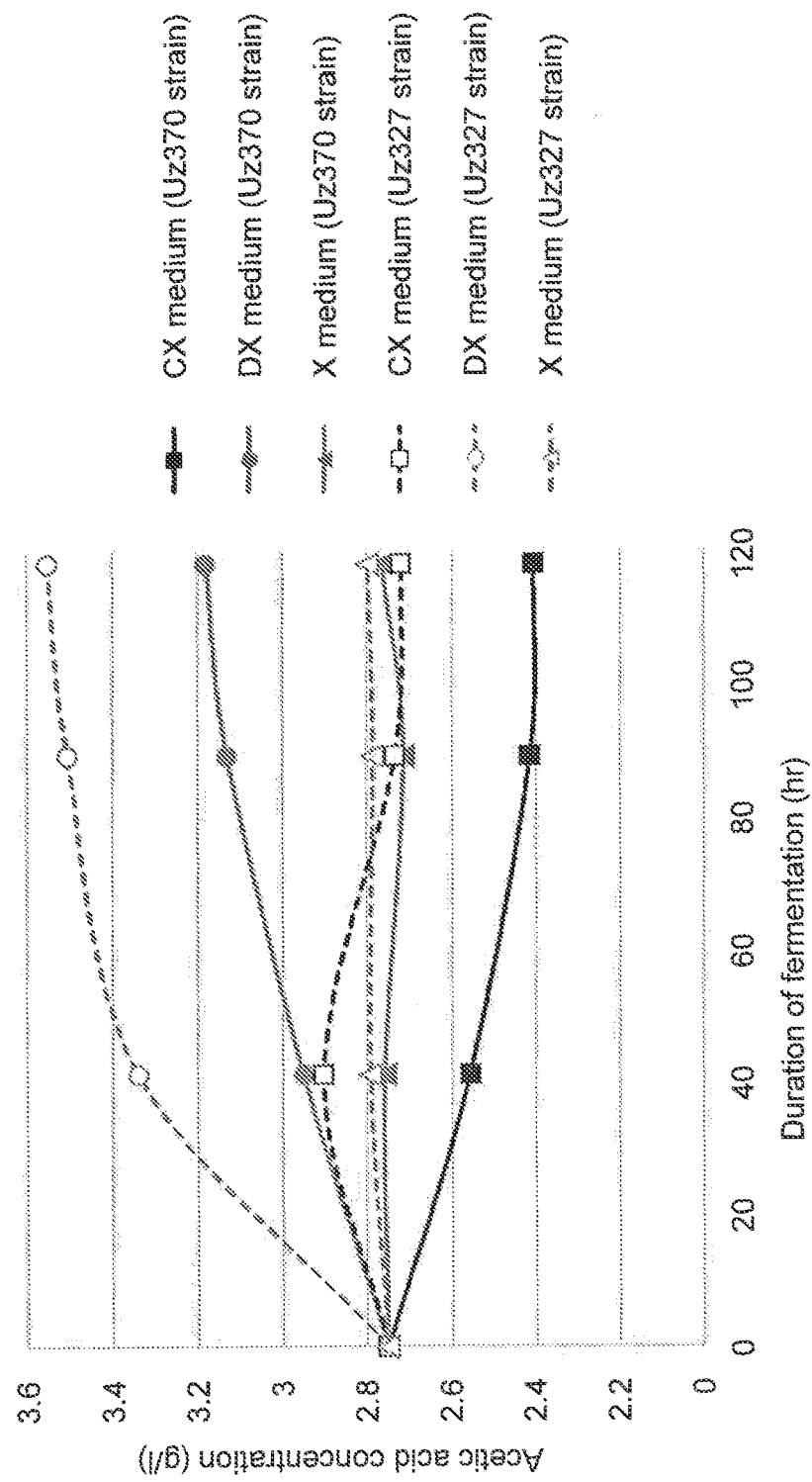
FIG. 2 is a characteristic diagram showing changes in acetic acid concentration in a medium.
Figure 3:
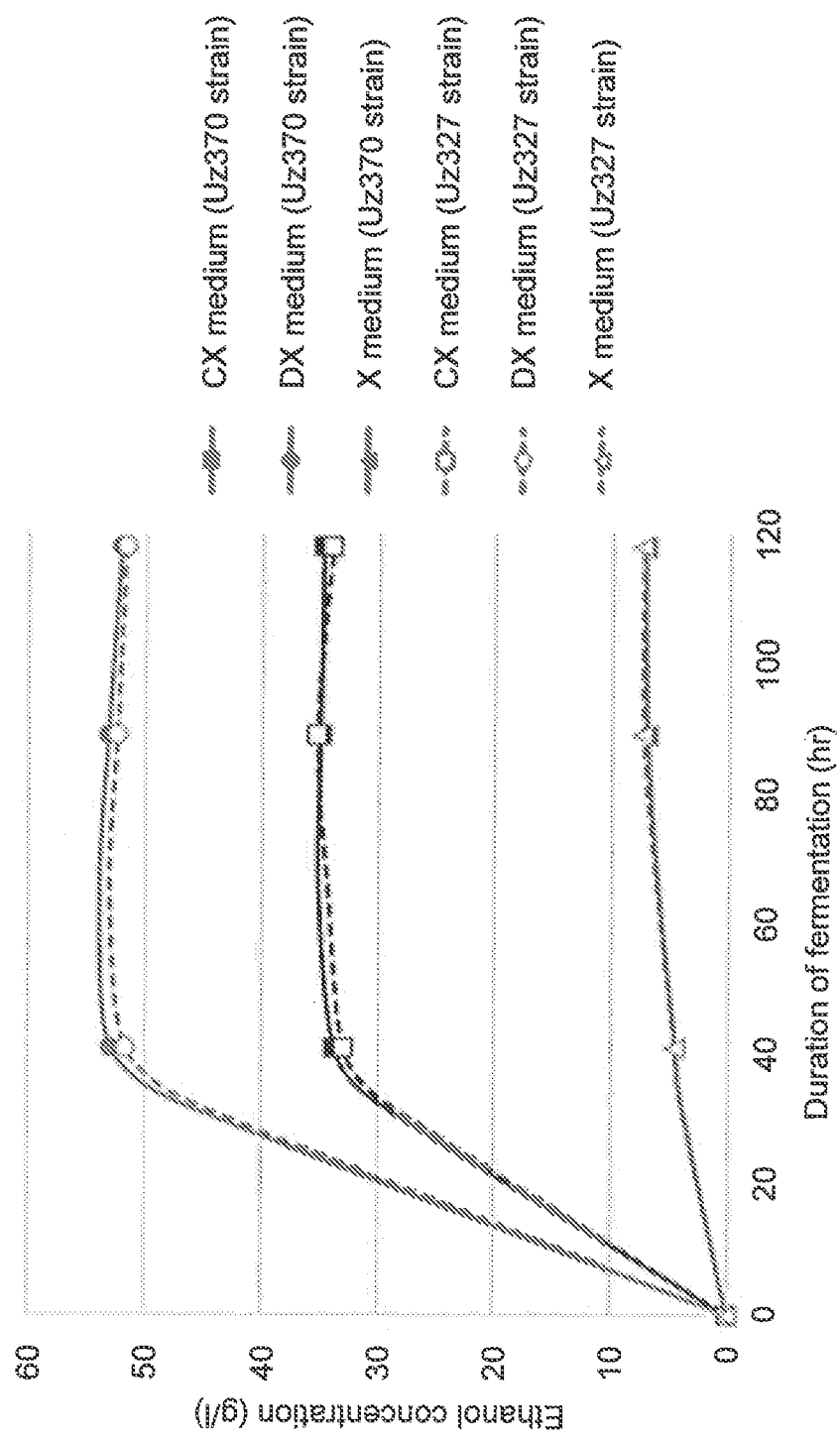
FIG. 3 is a characteristic diagram showing changes in ethanol concentration in a medium.
Figure 4:
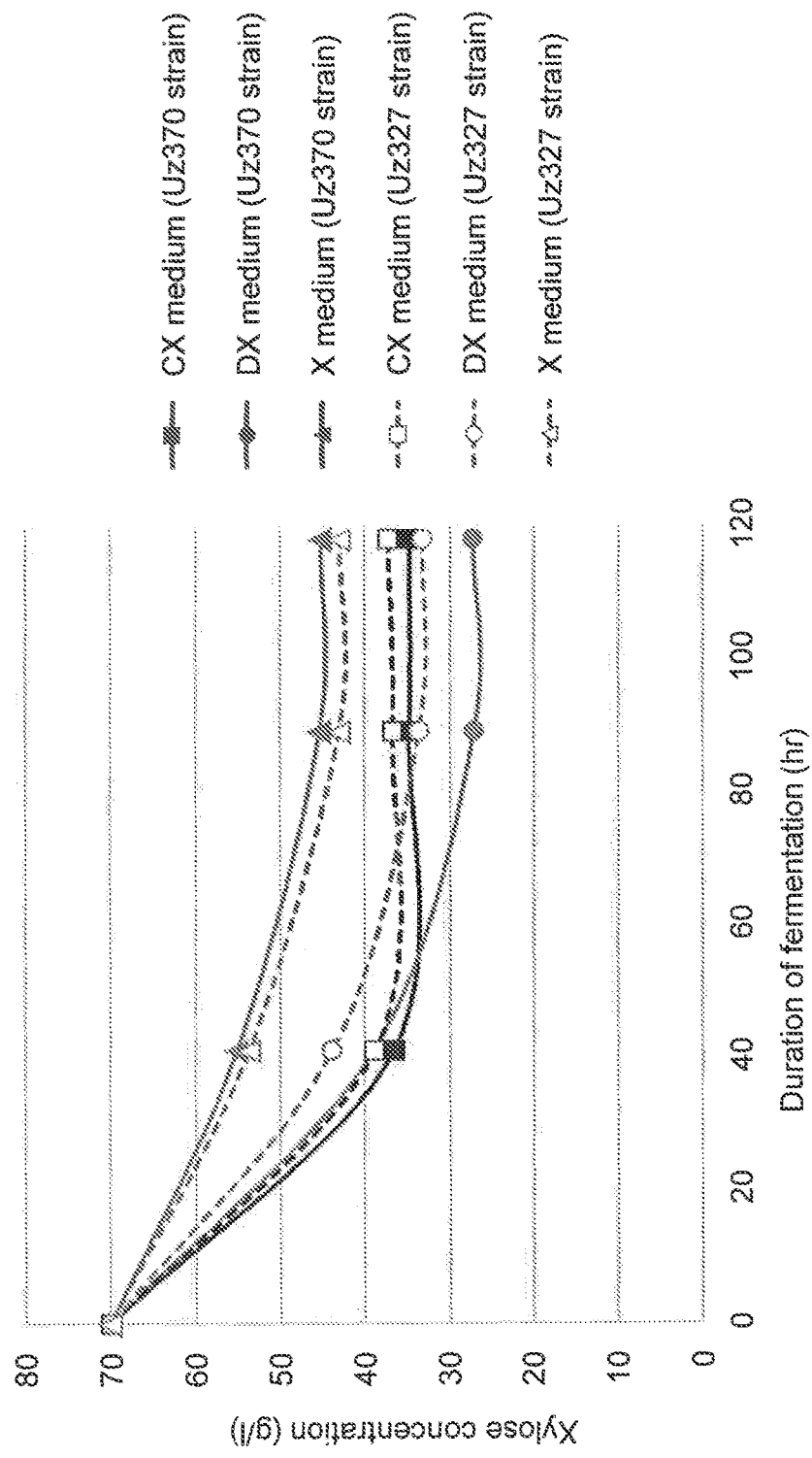
FIG. 4 is a characteristic diagram showing changes in xylose concentration in a medium.

As the results of the fermentation test, FIG. 2 shows changes in acetic acid concentration in a medium, FIG. 3 shows changes in ethanol concentration in a medium, and FIG. 4 shows changes in xylose concentration in a medium. As shown in FIG. 2, the Uz370 strain overexpressing the mhpF gene was capable of metabolizing acetic acid in a medium only when a CX medium for simultaneous saccharification and fermentation was used. In contrast, the Uz370 strain did not metabolize acetic acid in a medium containing glucose and xylose or a medium containing xylose alone as saccharide sources. When a medium containing glucose and xylose (i.e., a DX medium) was used, as shown in FIG. 2, the Uz370 strain overexpressing the mhpF gene was evaluated as producing a reduced amount of acetic acid, compared with the Uz327 strain. However, acetic acid production caused with the elapse of fermentation time was evaluated as substantially equivalent to that of the Uz327 strain. The Uz370 strain overexpressing the mhpF gene was evaluated as equivalent to the Uz327 strain in terms of ethanol yield or xylose metabolism activity, as shown in FIG. 3 and FIG. 4.

Reference Example 1

In Reference Example 1, a process for preparing pCR-5U_PDC6-T_HIS3-P_TDH3-Ble-T_URA3-PDC1part- 5U_PDC6 used in the examples is described. At the outset, a DNA fragment containing a 5' upstream untranslated region of the PDC6 gene and a part of the PDC6 gene was amplified using the genome of the OC2 yeast strain as a template, the amplified fragment was subjected to cloning with the use of the Zero Blunt TOPO PCR Cloning Kit, and the resultant was designated as pCR-5U_PDC6. A pair of PCR primers TB0948 (5'-GTTGAAGTCGCCTGG-TAGCC-3': SEQ ID NO: 15) and TB0735 (5'-CGGTGATC-CCCTTGAAAAAG-3': SEQ ID NO: 16) was used.

Also, a DNA fragment containing a terminator region of the HIS3 gene, a DNA fragment containing a promoter region of the TDH3 gene, a DNA fragment containing a terminator region of the URA3 gene, and a DNA fragment containing a part of the PDC1 gene were amplified by PCR using the genome of the OC2 yeast strain as a template.

The DNA fragment containing a terminator region of the HIS3 gene was amplified by PCR using, as primers, TB1401 (5'-TGCGGCCGGCCGCAGC-3': SEQ ID NO: 17) and TB1433 (5'-CGCTAACATTCAACGCTAAGAGCGCGC-CTCGTTC-3': SEQ ID NO: 18). The DNA fragment containing a promoter region of the TDH3 gene was amplified by PCR using, as primers, TB2717 (5'-TAGCGTTGAAT-GTTAGCGTCAACAAC-3': SEQ ID NO: 19) and TB1928 (5'-TTTGTTTGTTTATGTGTGTTTATTCGAAAC-3': SEQ ID NO: 20). The DNA fragment containing a terminator region of the URA3 gene was amplified by PCR using, as primers, TB2121 (5'-TGCATGTCTACTAAACTCA-CAAATTAGAGCTTCAATT-3': SEQ ID NO: 21) and TB1672 (5'-GTCGACCAAGTTAGCTGGGGG-TAATAACTGATATAATTAAA-3': SEQ ID NO: 22). The DNA fragment containing a part of the PDC1 gene was amplified by PCR using, as primers, TB2814 (5'-CCA-GCTAACTTGGTCGACTTG-3': SEQ ID NO: 23) and TB0115 (5'-TTGCAAAGAACCGTCACCAATG-3': SEQ ID NO: 24).

In addition, the phleomycin-resistant gene was amplified by PCR using pBBLE-LDHKCB (Applied and Environmental Microbiology, 71, 2789-2792) as a template. A pair of PCR primers TB2100 (5'-ACATAAACAAACAAAAT-GACCGACCAAGCGACG-3': SEQ ID NO: 25) and TB0897 (5'-AGTTTAGTAGACATGCATCATGAGATGC-CTGCAAG-3': SEQ ID NO: 26) was used.

Further, a DNA fragment linearized upon cleavage at a site approximately 700 bp upstream from the 5' end of the PDC6 gene was amplified by PCR using pCR-5U_PDC6 as a template. A pair of PCR primers TB2105 (5'-CTGCGGC-CGGCCGCACTTCCAAGCATCTCATAAACC-3': SEQ ID NO: 27) and TB4031 (5'-ACATAAACAAACAAAGAT-GTACGATCGCCTGCAC-3': SEQ ID NO: 28) was used. The DNA fragment obtained by PCR, the DNA fragment containing a terminator region of the HIS3 gene, and the DNA fragment containing a promoter region of the TDH3 gene were subjected to cloning using the In-Fusion™ Advantage PCR Cloning Kit, and the resulting plasmid was designated as pCR-5U_PDC6-T_HIS3-P_TDH3-3U_PDC6.

Subsequently, a DNA fragment linearized upon cleavage at a site between the promoter region of the TDH3 gene and the 5' upstream untranslated region of the PDC6 gene was amplified by PCR using pCR-5U_PDC6-T_HIS3-P_TDH3-5U_PDC6 obtained above as a template. A pair of PCR primers TB1928 (5'-TTTGTTGTTTATGTGTGTTTATTC-GAAAC-3': SEQ ID NO: 29) and TB2118 (5'-GACGGT-TCTTTGCAAGATGTACGATCGCCTGCAC-3': SEQ ID NO: 30) was used. The DNA fragment obtained by PCR, the DNA fragment containing a terminator region of the URA3 gene, the phleomycin-resistant gene, and the DNA fragment containing a part of the PDC1 gene were subjected to cloning using the In-Fusion™ Advantage PCR Cloning Kit, and the resulting plasmid was designated as pCR-5U_PDC6-T_HIS3-P_TDH3-Ble-T_URA3-PDC1part-5U_PDC6.

In Reference Example 1, also, pCR-T_HIS3-P_TDH3-AUR1-C-P_TDH2-IDP2m-T_IDP2-PDC1part used in the examples was prepared using pCR-5U_PDC6-T_HIS3-P_TDH3-Ble-T_URA3-PDC1part-5U_PDC6 prepared in the manner described above. At the outset, a DNA fragment containing a terminator region of the HIS3 gene and a promoter region of the TDH3 gene was amplified by PCR using pCR-5U_PDC6-T_HIS3-P_TDH3-Ble-T_URA3-PDC1part-5U_PDC6 as a template. A pair of PCR primers TB3345 (5'-TGCGGCCGGCCGCAGCTTTGCAGAG-3': SEQ ID NO: 31) and TB1928 was used.

Separately, a DNA fragment containing a promoter region of the TDH2 gene, a DNA fragment containing a mitochondrial translocation signal of the COX4 gene, a DNA fragment containing ORF and a terminator region of the IDP2 gene, and a DNA fragment containing a part of the PDC1 gene were amplified by PCR using the genome of the OC2 yeast strain (NBRC2260) as a template. These primers used for PCR were designed with reference to the DNA sequence data stored in the *Saccharomyces* Genome Database (http://www:yeastgenome.org/), in such a manner that the amplified DNA fragments would overlap each other by about 15 bp. The DNA fragment containing a promoter region of the TDH2 gene was amplified by PCR using, as primers, TB2704 (5'-CTTGACGGGTATTCTGAGCATCTTAC-3': SEQ ID NO: 32) and TB2595 (5'-TTTGTTTTGTTTGTTT-GTGTGATGAATTTAATTTG-3': SEQ ID NO: 33). The DNA fragment containing a mitochondrial translocation signal of the COX4 gene was amplified by PCR using, as primers, TB2448 (5'-AACAAACAAAACAAAAT-GCTTTCACTACGTCAATC-3': SEQ ID NO: 34) and TB2449 (5'-CTTAATCTTTGTCATAAGAGCATATCTA-GAGCTACACAAAG-3': SEQ ID NO: 35). The DNA fragment containing ORF and a terminator region of the IDP2 gene was amplified by PCR using, as primers, TB2452 (5'-ATGACAAAGATTAAGGTAGCTAACCCC-3': SEQ ID) NO: 36) and TB2092 (5'-GACCAAGTTAGCTGG-TATATCGGTCCTCTGTGTAG-3': SEQ ID NO: 37). The DNA fragment containing a part of the PDC1 gene was amplified by PCR using, as primers, TB2814 and TB0115.

The mitochondrial translocation signal sequence of the COX4 gene was predicted as a sequence comprising 25 amino acids at the 5' terminus of ORF using the prediction program "TargetP" based on the algorism of O. Emanuelsson et al. (J. Mol. Biol., 300, 1005-1016) (http://www.cb-s.dtu.dk/services/TargetP/).

A DNA fragment containing ORF and a terminator region of the AUR1-C (Aureobasidin-resistant) gene was amplified by PCR using pAUR101(Takara Bio) as a template. A pair of PCR primers TB1972 (5'-ACATAAACAAACAAAATG-GCAAACCCTTTTTCGAGATG-3': SEQ ID NO: 38) and TB1973 (5'-AGAATACCCGTCAAGCTGGATAGAGCCT-CATCGTTAC-3': SEQ ID NO: 39) was used.

Subsequently, the DNA fragment containing an AUR1-C gene and the DNA fragment containing a promoter region of the TDH2 gene amplified by PCR were allowed to bind to each other using the In-Fusion™ Advantage PCR Cloning Kit (Clontech), and the resultant was amplified by PCR using, as primers, TB1972 and TB2595. The DNA fragment containing a mitochondrial translocation signal of the COX4 gene, the DNA fragment containing ORF and a terminator region of the IDP2 gene, and the DNA fragment containing a part of the PDC1 gene were allowed to bind to one another using, as primers, TB2448 and TB0115, and the resultant was amplified by PCR. These two bound DNA fragments were cloned into a plasmid using the Zero Blunt TOPO PCR Cloning Kit (Invitrogen). With the use of the cloned plasmid as a template, the two DNA fragments amplified by PCR were allowed to bind to the DNA fragment containing the terminator region of the HIS3 gene and the promoter region of the TDH3 gene using the In-Fusion™ Advantage PCR Cloning Kit, and the bound DNA fragments were amplified by PCR using, as primers, TB1932 and TB0115. The bound DNA fragments amplified by PCR were cloned into a plasmid using the Zero Blunt TOPO PCR Cloning Kit. The resultant was designated as pCR-T_HIS3-P_TDH3-AUR1-C-P_TDH2-IDP2m-T_IDP2-PDC1 part.

Reference Example 2

In Reference Example 2, a process for producing a strain resulting from heterozygous introduction of XYL1, XYL2, and XKS1 gene overexpression and GRE3 gene disruption into a homothallic diploid yeast strain; i.e., the *Saccharomyces cerevisiae* OC2-T strain (Saitoh, S. et al., J. Ferment. Bioeng., 1996, Vol. 81, pp. 98-103), is described.
<Preparation of DNA Fragment for Overexpression of XYL1, XYL2, and XKS1 Genes and Disruption of GRE3 Gene>

A DNA fragment containing the GRE3 gene and its 5' upstream and 3' downstream untranslated regions was amplified by PCR using the genomic DNA of the BY4742 yeast strain (Open Biosystems) as a template. A pair of PCR primers TB2358 (5'-TGGGAATATTACCGCTCGAAG-3': SEQ ID NO: 40) and TB2359 (5'-AAGGGGGAAGGT-GTGGAATC-3': SEQ ID NO: 41) was used. PCR primers used for amplification of the DNA sequence of the BY4742 yeast strain were designed with reference to the DNA sequence data stored in the *Saccharomyces* Genome Database. With the use of the pUC19 plasmid as a template, a linear DNA fragment containing full-length pUC19 that seemed to have been cleaved at the pUC19 multicloning site was amplified by PCR. A pair of PCR primers TB2373 (5'-CACACCTTCCCCCTTGATCCTCTAGAGTCGACC-3': SEQ ID NO: 42) and TB2374 (5'-GCGGTAATATTC-CCAGATCCCCGGGTACCGAGCTC-3': SEQ ID NO: 43) was used. The two above DNA fragments were subjected to cloning using the In-Fusion™ Advantage PCR Cloning Kit (Takara Bio), and the resultant was designated as pUC19-5U_GRE3-GRE3-3U_GRE3.

With the use of pUC19-5U_GRE3-GRE3-3U_GRE3 as a template, the DNA fragment containing the GRE3 gene, its 5' upstream and 3' downstream untranslated regions, and pUC19 was amplified by PCR. With the use of genomic DNA of the BY4742 yeast strain as a template, the DNA fragment containing the TEF1 promoter region and the DNA fragment containing the XKS1 gene and the HIS3 terminator region were amplified by PCR. A pair of PCR primers TB3018 (5'-AACGAGGCGCGCTCTTCCAGCCAG-TAAATCCA-3': SEQ ID) NO: 44) and TB3017 (5'-GC-TATGGTGTGTGGGTGCTTTAAAAAATTTC-CAATTTTCCTTTACG-3': SEQ ID NO: 45), that of TB2210 (5'-CCCACACACCATAGCTTCAAAATG-3': SEQ ID NO: 46) and TB2269 (5'-TCTTTAGATTAGATT-GCTATGCTTTCTTTCTAATGAGCAAG-3': SEQ ID NO: 47), that of TB2345 (5'-AATCTAATCTAAAGAATGTTGT-GTTCAGTAATTCAGAGAC-3': SEQ ID NO: 48) and TB2346 (5'-CTGCGGCCGGCCGCATTAGAT-GAGAGTCTTTTCCAGTTC-3': SEQ ID NO: 49), and that of TB1401 (5'-TGCGGCCGGCCGCAGC-3': SEQ ID NO: 50) and TB2683 (5'-GCGCCTCGTTTCAGAATGA-3': SEQ ID NO: 51) were used, respectively.

The four above types of DNA fragments were subjected to cloning using the In-Fusion™ Advantage PCR Cloning Kit, and the resultant was designated as pUC19-5U_GRE3-P_TEF1-XKS1-T_HIS3-3U_GRE3.

With the use of pUC19-5U_GRE3-P_TEF1-XKS1-T_HIS3-3U_GRE3 as a template, a linear DNA fragment containing a full-length plasmid that seemed to have been cleaved between the HIS3 terminator region and the 3' downstream untranslated region of the GRE3 gene was amplified by PCR. With the use of the genomic DNA of the BY4742 yeast strain as a template, a DNA fragment containing the TDH2 promoter region and a DNA fragment containing the ILV3 terminator region were amplified by PCR. With the use of the genomic DNA of *Pichia stipitis* as a template, the XYL1 gene was amplified by PCR. A pair of PCR primers TB9020 (5'-TCCAGCCAGTAAAATC-CATAC-3': SEQ ID NO: 52) and TB2457 (5'-CCGT-CAAGAGAGCGCGCCTCGTTCAG-3': SEQ ID NO: 53), that of TB2844 (5'-GCGCTCTCTTGACGGGTATTCT-GAGCATCTTAC-3': SEQ ID NO: 54) and TB2595 (5'-TTTGTTTTGTTTGTTTGTGTGATGAATTAATTG-3': SEQ ID NO: 55), that of TB2314 (5'-AACAAACAAAACAAAATGCCTTCTATTAAGTT-GAAC-3': SEQ ID NO: 56) and TB2455 (5'-GGGGC-CTATAATGCATTAGACGAAGATAGGAATCTTG-3': SEQ ID NO: 57), and that of TB2456 (5'-AACAAACAAAACAAAATGCCTTCTATTAAGTT-GAAC-3': SEQ ID NO: 58) and TB3019 (5'-ATTTTACTG-GCTGGAATTTCGTAGATTATAATTAAGGCGAC-3': SEQ ID NO: 59) were used, respectively. PCR primers used for amplification of the XYL1 gene sequence were designed with reference to the XYL1 gene of *Pichia stipitis* registered with GeneBank (Accession Number: XM_001385144). The four above types of DNA fragments were subjected to cloning using the In-Fusion™ Advantage PCR Cloning Kit, and the resultant was designated as pUC19-5U_GRE3-P_TEF1-XKS1-T_HIS3-P_TDH2-XYL1-T_ILV3-3U_GRE3.

With the use of pUC19-5U_GRE3-P_TEF1-XKS1-T_HIS3-P_TDH2-XYL1-T_ILV3-3U_GRE3 as a template, a linear DNA fragment containing a full-length plasmid that seemed to have been cleaved between the ILV3 terminator region and the 3' downstream untranslated region of the GRE3 gene was amplified by PCR. With the use of the genomic DNA of the BY4742 yeast strain as a template, a DNA fragment containing the PDC1 promoter region and a DNA fragment containing the ILV6 terminator region were amplified by PCR. With the use of the genomic DNA of *Pichia stipitis* as a template, the XYL2 gene was amplified by PCR. A pair of PCR primers TB2375 (5'-AGTTGCTT-GACACGGTGGAAGAAGGTCCAGCCAGTAAAATC-CATA-3': SEQ ID NO: 60) and TB3021 (5'-ATTTCGTA-GATTATAATTAAGGCGAC-3': SEQ ID NO: 61), that of TB2010 (5'-TTTGATTGATTTGACTGTGTTATTTTGC-3': SEQ ID) NO: 62) and TB2261 (5'-CCGTGT-CAAGCAAGCAACTATGGG-3': SEQ ID NO: 63), that of TB3022 (5'-TATAATCTACGAAATTAATAAGAAAGGT-GACCGTG-3': SEQ ID NO: 64) and TB2347 (5'-GT-TAGTCTCTGGCCTTGCG-3': SEQ ID NO: 65), and that of TB2351 (5'-GGCCGAGAGACTAACTTACTCAGGGC-CGTCAAT-3': SEQ ID NO: 66) and TB2352 (5'-GT-CAAATCAATCAAAATGACTGCTAACCCCTCC-3': SEQ ID NO: 67) were used, respectively. PCR primers used for amplification of the XYL2 gene sequence were designed with reference to the XYL2 gene of *Pichia stipitis* registered with GeneBank (Accession Number: AF127801 or X55392). The four above types of DNA fragments were subjected to cloning using the In-Fusion™ Advantage PCR Cloning Kit, and the resultant was designated as pUC19-5U_GRE3-P_TEF1-XKS1-T_HIS3-P_TDH2-XYL1-T_ILV3-ILV6_T-XYL2-P DC1_P-3U_GRE3.

With the use of pUC19-5U_GRE3-P_TEF1-XKS1-T_HIS3-P_TDH2-XYL1-T_ILV3-ILV6_T-XYL2-P DC1_P-3U_GRE3 as a template, a DNA fragment comprising a region from the 5' upstream untranslated region to the 3' downstream untranslated region of the GRE3 gene was amplified by PCR. The resulting fragment was used for preparation of a strain overexpressing the XYL1, XYL2, and XKS1 genes and disrupting the GRE3 gene.

<Preparation of Strain Overexpressing XYL1, XYL2, and XKS1 Genes and Hetero-Disrupting GRE3 Gene>

With the use of the DNA fragment for overexpression of the XYL1, XYL2, and XKS1 genes and disruption of the GRE3 gene, the OC2-T strain was transformed using the Frozen-EZ Yeast Transformation II kit (ZYMO RESEARCH) in accordance with the protocols included in the kit. Thereafter, the strain was inoculated on a plate using xylose as a single carbon source and then cultured at 30 degrees C. for 7 days to obtain a transformant. Genomic DNA was prepared from the transformant, PCR was carried out using primers located at the outside of the inserted DNA fragment and at the inside of the vector; i.e., TB2356 (5'-TGGGGCTAAACGAGATTTGG-3': SEQ ID NO: 68) and TB592 (5'-GAAATTTAGTATGCTGTGCTTGGG-3': SEQ ID NO: 69), so as to confirm that a copy of the DNA of interest had been normally incorporated into the chromosome.

Example 2

In Example 2, a recombinant yeast strain was prepared through introduction of the acetaldehyde dehydrogenase gene (the mhpF gene) and the alcohol dehydrogenase gene (the ADH1 gene) derived from *E. coli* into a xylose-assimilating yeast strain and through disruption of the alcohol dehydrogenase gene (the ADH2 gene) thereof, and acetic acid-metabolizing ability of the recombinant yeast strain was evaluated. The alcohol dehydrogenase gene (the ADH1 gene) to be introduced encodes a protein having activity of converting acetaldehyde into ethanol. The alcohol dehydrogenase gene (the ADH1 gene) to be disrupted encodes a protein having activity of converting ethanol into acetaldehyde.

<Test Strains>

In Example 2, the Uz326 strain prepared in Example 1, the histidine-requiring Uz644 strain derived from the Uz326 strain, the uracil-requiring Uz659 strain selected from among Uz644 strains grown in a medium supplemented with 5-fluoroorotic acid (Boeke, J. D., et al., 1987, Methods Enzymol.; 154: 164-75), the Uz670 strain derived from the Uz659 strain by introduction of the mhpF gene, the Uz672 strain derived from the Uz659 strain by introduction of the mhpF gene and the ADH1 gene, the Uz822 strain derived from the Uz659 strain by introduction of the ADH1 gene, the Uz674 strain derived from the Uz659 strain by disruption of the ADH2 gene, the Uz669 strain derived from the Uz659 strain by disruption of the ADH2 gene and introduction of the mhpF gene, and the Uz737 strain derived from the Uz659 strain by disruption of the ADH2 gene and introduction of the mhpF gene and the ADH1 gene were constructed (Table 1).

| Strain | Genotype |
|---|---|
| Uz326 | GRE3:: $P_{TDH2}$-XYL1 $P_{PDC1}$-XYL2 $P_{TEF1}$-XKS1 trp1::URA3 |
| Uz644 | his3::AUR1-C GRE3:: $P_{TDH2}$-XYL1 $P_{DC1}$-XYL2 $P_{TEF1}$-XKS1 trp1::URA3 |
| Uz659 | his3::AUR1-C GRE3:: $P_{TDH2}$-XYL1 $P_{PDC1}$-XYL2 $P_{TEF1}$-XKS1 trp1 ura3 |
| Uz670 | mhpF HIS3 his3::AUR1-C GRE3:: $P_{TDH2}$-XYL1 $P_{PDC1}$-XYL2 $P_{TEF1}$-XKS1 trp1 ura3 |
| Uz672 | mhpF ADH1 HIS3 his3::AUR1-C GRE3:: $P_{TDH2}$-XYL1 $P_{PDC1}$-XYL2 $P_{TEF1}$-XKS1 trp1 ura3 |
| Uz822 | ADH1 HIS3 his3::AUR1-C GRE3:: $P_{TDH2}$-XYL1 $P_{PDC1}$-XYL2 $P_{TEF1}$-XKS1 trp1 ura3 |
| Uz674 | adh2::H1S3 his3::AUR1-C GRE3:: $P_{TDH2}$-XYL1 $P_{PDC1}$-XYL2 $P_{TEF1}$-XKS1 trp1 ura3 |
| Uz669 | adh2::mhpF HIS3 his3::AUR1-C GRE3:: $P_{TDH2}$-XYL1 $P_{PDC1}$-XYL2 $P_{TEF1}$-XKS1 trp1 ura3 |
| Uz737 | adh2::mhpF ADH1 HIS3 his3::AUR1-C GRE3:: $P_{TDH2}$-XYL1 $P_{PDC1}$-XYL2 $P_{TEF1}$-XKS1 trp1 ura3 |
| Uz996 | adh2::TRP1 |

<Preparation of DNA Fragment for Disruption of HIS3 Gene>

A DNA fragment containing the HIS3 gene and its 5' upstream and 3' downstream untranslated regions was amplified by PCR using the genomic DNA of the OC2 yeast strain as a template. A pair of PCR primers TB3164 and TB3165 was used (hereafter, the primers used in the examples are collectively shown in Table 2). The amplified fragment was cloned into a plasmid using the Zero Blunt TOPO PCR Cloning Kit (Life Technologies Corporation), and the resultant was designated as pCR-5U_HIS3-HIS3-3U_HIS3.

With the use of pCR-5U_HIS3-HIS3-3U_HIS3 as a template, a DNA fragment containing the 5' upstream and 3' downstream untranslated regions of the HIS3 gene pCR-BluntII-TOPO was amplified by PCR. With the use of pAUR101 (Takara Bio) as a template, a DNA fragment containing the AUR1-C gene and its promoter and terminator regions was amplified by PCR. A pair of PCR primers TB3458 and TB3459 and that of TB2885 and TB2859 designed in such a manner that the amplified DNA fragments would overlap each other by about 15 bp were used, respectively. The DNA fragments were subjected to cloning using the In-Fusion HD Cloning Kit (Takara Bio), and the resultant was designated as pCR-5U_HIS3-AUR1-C-3U_HIS3.

<Preparation of Strain Disrupting HIS3 Gene>

A DNA fragment excluding the pCR-Blunt II TOPO vector portion was amplified by PCR using pCR-5U_HIS3-AUR1-C-3U_HIS3 as a template, so as to prepare a DNA fragment for disruption of the HIS3 gene. A pair of PCR primers TB3164 and TB3165 was used. With the use of the DNA fragment thus prepared, the Uz326 strain overexpressing xylose-assimilating genes (i.e., XYL1, XYL2, and XKS1) (Example 1) was transformed into the homothallic diploid yeast strain; i.e., the *Saccharomyces cerevisiae* OC2-T strain, using the Frozen-EZ Yeast Transformation II kit (ZYMO RESEARCH) in accordance with the protocols included in the kit. Thereafter, the resultant was seeded on a YPD plate containing Aureobasidin, and culture was conducted at 30 degrees C. for 7 days to obtain a transformant. The resulting strain was allowed to sporulate in a sporulation medium (1% potassium phosphate, 0.1% yeast extract, 0.05% glucose, and 2% agar), so as to cause diploidization with the utilization of homothallic properties. A diploid strain containing the AUR1-C gene integrated into and the HIS3 gene disrupted in the HIS3 genetic loci of its chromosome was obtained. The resultant was designated as the Uz644 strain.

<Preparation of ADH2 Gene-Disrupting DNA Fragment (HIS3 Marker)>

A DNA fragment containing the ADH2 gene and its 5' upstream and 3' downstream untranslated regions was amplified by PCR using the genomic DNA of the BY4742 yeast strain as a template. A pair of PCR primers TB2939 and TB2940 was used. The amplified fragment was cloned into a plasmid using the Zero Blunt TOPO PCR Cloning Kit, and the resultant was designated as pCR-5U_ADH2-ADH2-3U_ADH2.

With the use of pCR-5U_ADH2-ADH2-3U_ADH2 as a template, a DNA fragment containing the ADH2 gene, its 5' upstream and 3' downstream untranslated regions, and a region containing pCR-BluntII-TOPO was amplified by PCR. With the use of pCR-5U_HIS3-HIS3-3U_HIS3 as a template, a DNA fragment containing the HIS3 gene and its promoter and terminator regions was amplified by PCR. A pair of PCR primers TB3100 and TB3102 and that of TB3101 and TB3089 designed in such a manner that the amplified DNA fragments would overlap each other by about 15 bp were used, respectively. The DNA fragments were subjected to cloning using the In-Fusion HD Cloning Kit (Takara Bio), and the resultant was designated as pCR-5U_ADH2-HIS3-3U_ADH2.

<Preparation of Strain Disrupting ADH2 Gene>

A DNA fragment excluding the pCR-Blunt II TOPO vector portion was amplified by PCR using pCR-5U_ADH2-HIS3-3U_ADH2 as a template, so as to prepare a DNA fragment disrupting the ADH2 gene. A pair of PCR primers TB2939 and TB2940 was used. The Uz644 strain was transformed with the use of the DNA fragment obtained. Thereafter, the resultant was seeded on a plate containing a histidine-free SC medium (Methods in Yeast Genetics, Cold Spring Harbor Laboratory Press), and culture was conducted at 30 degrees C. for 7 days to obtain a transformant. The resulting strain was allowed to sporulate to cause diploidization. A diploid strain containing the HIS3 gene integrated into and the ADH2 gene disrupted in the ADH2 genetic loci of its chromosome was obtained. The resultant was designated as the Uz674 strain.

<Preparation of DNA Fragment for Overexpression of mhpF Gene>

With the use of pCR-T_HIS3-P_TDH3-AUR1-C-ERO1_T-mhpF-HOR7_P-PDC1part (see Example 1) as a template, a DNA fragment containing a terminator region of the ERO1 gene, the mhpF gene, and a promoter region of the HOR7 gene was amplified by PCR. A pair of PCR primers TB3598 and TB2654 was used. With the use of genomic DNA of the BY4742 strain as a template, a DNA fragment containing a terminator region of the CYC1 gene was amplified by PCR. A pair of PCR primers TB2236 and TB3597 was used. With the use of pCR-5U_HIS3-HIS3-3U_HIS3 as a template, a DNA fragment containing the HIS3 gene and its promoter and terminator regions was amplified by PCR. A pair of PCR primers TB3099 and TB3089 was used. With the use of pCR-5U_ADH2-ADH2-3U_ADH2 as a template, a DNA fragment linearized upon cleavage at a site between the ADH2 gene and a 3' downstream untranslated region was amplified by PCR. A pair of PCR primers TB3172 and TB3100 was used. The pair of primers was designed in such a manner that the amplified DNA fragments would overlap each other by about 15 bp.

The four above types of DNA fragments were subjected to cloning using the In-Fusion HD Cloning Kit, and the resultant was designated as pCR-5U_ADH2-ADH2-T_CYC1-ERO1_T-mhpF-HOR7_P-HIS3-3U_ADH2.

<Preparation of Strain Overexpressing mhpF Gene>

With the use of pCR-5U_ADH2-ADH2-T_CYC1-ERO1_T-mhpF-HOR7_P-HIS3-3U_ADH2 as a template, a DNA fragment excluding the pCR-Blunt II TOPO vector portion was amplified by PCR to prepare a DNA fragment for overexpression of the mhpF gene. A pair of PCR primers TB3326 and TB2940 was used. The Uz644 strain was transformed using the DNA fragment obtained. Thereafter, the resultant was seeded on a plate containing a histidine-free SC medium, and culture was conducted at 30 degrees C. for 5 days to obtain a transformant. The resulting strain was allowed to sporulate to cause diploidization. A diploid strain containing the mhpF genes integrated into the ADH2 genetic loci of its chromosome was obtained and designated as the Uz670 strain.

<Preparation of DNA Fragment for Overexpression of mhpF and ADH1 Genes>

With the use of pCR-5U_ADH2-ADH2-T_CYC1-ERO1-T-mhpF-HOR7_P-HIS3-3U_ADH2 as a template, a DNA fragment linearized upon cleavage at a site between a terminator region of the CYC1 gene and a terminator region of the ERO1 gene was amplified by PCR. A pair of PCR primers TB3173 and TB2429 was used. With the use of genomic DNA of the BY4742 strain as a template, a DNA fragment containing a promoter region of the TDH3 gene and a DNA fragment containing the ADH1 gene and a part of its terminator region were amplified by PCR. A pair of PCR primers TB2717 and TB1938 and that of TB2997 and TB2998 were used, respectively. The pairs of primers were designed in such a manner that the amplified DNA fragments would overlap each other by about 15 bp. The three above types of DNA fragments were subjected to cloning using the In-Fusion HD Cloning Kit, and the resultant was designated as pCR-5U_ADH1-2-ADH2-T_CYC1-P_TDH3-ADH1-T_ADH1-ERO1_T-mhpF-HOR7_P-HIS3-3U_ADH2.

<Preparation of Strain Overexpressing mhpF and ADH1 Genes>

With the use of pCR-5U_ADH2-ADH2-T_CYC1-P_TDH3-ADH1-T_ADH1-ERO1_T-mhpF-HOR7_P-HIS3-3U_ADH2 as a template, a DNA fragment excluding the pCR-Blunt II TOPO vector portion was amplified by PCR to prepare a DNA fragment for overexpression of the mhpF gene and the ADH1 gene. A pair of PCR primers TB3326 and TB2940 was used. The Uz644 strain was transformed using the DNA fragment obtained. Thereafter, the resultant was seeded on a plate containing a histidine-free SC medium, and culture was conducted at 30 degrees C. for 5 days to obtain a transformant. The resulting strain was allowed to sporulate to cause diploidization. A diploid strain containing the mhpF gene and the ADH1 gene integrated into sites in the vicinity of the ADH2 genetic loci of its chromosome was obtained and designated as the Uz672 strain.

<Preparation of DNA Fragment for Overexpression of mhpF and ADH1 Genes and Disruption of ADH2 Gene>

With the use of pCR-5U_ADH2-ADH2-T_CYC1-P_TDH3-ADH1-T_ADH2-ERO1_T-mhpF-HOR7_P-HIS3-3U_ADH2 as a template, a DNA fragment excluding the ADH2 gene was amplified by PCR. A pair of PCR primers TB2717 and TB2943 was used. The pair of primers was designed in such a manner that the amplified DNA fragments would overlap each other by about 15 bp at both ends.

The fragment was transformed into an E. coli cell, a plasmid with a circular DNA fragment was obtained, and the resultant was designated as pCR-5U_ADH2-T_CYC1-P_TDH3-ADH1-T_ADH1-ERO1 T-mhpF-HOR7_P-HIS3-3U_ADH2.

<Preparation of Strain Overexpressing mhpF and ADH1 Genes and Disrupting ADH2 Gene>

With the use of pCR-5U_ADH2-T_CYC1-P_TDH3-ADH1-T_ADH1-ERO1_T-mhpF-HOR7_P-HIS3-3U_ADH2 as a template, a DNA fragment excluding the pCR-Blunt II TOPO vector portion was amplified by PCR to prepare a DNA fragment for overexpression of the mhpF gene and the ADH1 gene and disruption of the ADH2 gene. A pair of PCR primers TB2939 and TB2940 was used. The Uz644 strain was transformed using the DNA fragment obtained. Thereafter, the resultant was seeded on a plate containing a histidine-free SC medium, and culture was conducted at 30 degrees C. for 5 days to obtain a transformant. The resulting strain was allowed to sporulate to cause diploidization. A diploid strain containing the mhpF gene and the ADH1 gene integrated into and the ADH2 gene disrupted in the ADH2 genetic loci of its chromosome was obtained and designated as the Uz737 strain.

<Preparation of DNA Fragment for Overexpression of mhpF Gene and Disruption of ADH2 Gene>

With the use of pCR-5U_ADH2-T_CYC1-P_TDH3-ADH1-T_ADH1-ERO1_T-mhpF-HOR7_P-HIS3-3U_ADH2 as a template, a DNA fragment excluding the ADH1 gene was amplified by PCR. A pair of PCR primers TB3217 and TB1928 was used. The pair of primers was designed in such a manner that the amplified DNA fragments would overlap each other by about 15 bp at both ends. The fragment was transformed into E. coli to obtain a plasmid with a circular DNA fragment, and the resultant was designated as pCR-5U_ADH2-T_CYC1-P_TDH3-T_ADH1-ERO1-T-mhpF-HOR7_P-HIS3-3U_ADH2.

<Preparation of Strain Overexpressing mhpF Gene and Disrupting ADH2 Gene>

With the use of pCR-5U_ADH2-T_CYC1-P_TDH3-T_ADH1-ERO1_T-mhpF-HOR7_P-HIS3-3U_ADH12 as a template, a DNA fragment excluding the pCR-Blunt II TOPO vector portion was amplified by PCR to prepare a DNA fragment for overexpression of the mhpF gene and disruption of the ADH2 gene. A pair of PCR primers TB2939 and TB2940 was used. The Uz644 strain was transformed using the DNA fragment obtained. Thereafter, the resultant was seeded on a plate containing a histidine-free SC medium, and culture was conducted at 30 degrees C. for 5 days to obtain a transformant. The resulting strain was allowed to sporulate to cause diploidization. A diploid strain containing the mhpF gene integrated into and the ADH2 gene disrupted in the ADH2 genetic loci of its chromosome was obtained. The resultant was designated as the Uz669 strain.

<Preparation of DNA Fragment for Overexpression of ADH1 Gene>

With the use of pCR-5U_ADH2-ADH2-T_CYC1-P_TDH3-ADH1-T_ADH1-ERO1 T-mhpF-HOR7_P-HIS3-3U_ADH2 as a template, a DNA fragment excluding the mhpF gene expression cassette was amplified by PCR. A pair of PCR primers TB3090 and TB3086 was used. The pair of primers was designed in such a manner that the amplified DNA fragments would overlap each other by about 15 bp at both ends. The fragment was transformed into an E. coli cell, a plasmid with a circular DNA fragment was obtained, and the resultant was designated as pCR-5U_ADH2-ADH2-T_CYC1-P_TDH3-ADH1-T_ADH1-HIS3-3U_ADH2.

<Preparation of Strain Overexpressing ADH1 Gene>

With the use of pCR-5U_ADH2-ADH2-T_CYC1-P_TDH3-ADH1-T_ADH1-HIS3-3U_ADH2 as a template, a DNA fragment excluding the pCR-Blunt II TOPO vector portion was amplified by PCR to prepare a DNA fragment for overexpression of the ADH1 gene. A pair of PCR primers TB3326 and TB2940 was used. The Uz644 strain was transformed using the DNA fragment obtained. Thereafter, the resultant was seeded on a plate containing a histidine-free SC medium, and culture was conducted at 30 degrees C. for 5 days to obtain a transformant. The resulting strain was allowed to sporulate to cause diploidization. A diploid strain containing the ADH1 genes integrated into sites in the vicinity of the ADH2 genetic loci of its chromosome was obtained and designated as the Uz822 strain.

<Preparation of DNA Fragment for Disruption of ADH2 (TRP1 Marker)>

With the use of pCR-5U_ADH2-HIS3-3U_ADH2 as a template, a DNA fragment excluding the HIS3 gene was amplified by PCR. A pair of PCR primers TB4481 and TB3435 was used. With the use of genomic DNA of the BY4742 yeast strain as a template, a DNA fragment containing the TRP1 gene and its 5' upstream and 3' downstream untranslated regions was amplified by PCR. A pair of PCR primers TB2799 and TB2800 was used. The pair of primers was designed in such a manner that the amplified DNA fragments would overlap each other by about 15 bp. The two above types of DNA fragments were subjected to cloning using the In-Fusion HD Cloning Kit, and the resultant was designated as pCR-5U_ADH2-TRP1-3U_ADH2.

<Preparation of ADH2 Gene Strain>

With the use of pCR-5U_ADH2-TRP1-3U_ADH2 as a template, a DNA fragment excluding the pCR-Blunt II TOPO vector portion was amplified by PCR to prepare a DNA fragment for disruption of the ADH2 gene. A pair of PCR primers TB2939 and TB2940 was used. With the use of the DNA fragment obtained, the OC2 yeast strain in which TPP1 has been disrupted; i.e., the OC2-T strain (Saitoh, S. et al., J. Ferment. Bioeng., 1996, 81, 98-103), was transformed. Thereafter, the resultant was seeded on a plate containing a tryptophan-free SC medium, and culture was conducted at 30 degrees C. for 5 days to obtain a transformant. The resulting strain was allowed to sporulate to cause diploidization. A diploid strain containing the TRP1 genes integrated into and the ADH2 gene disrupted in the ADH2 genetic loci of its chromosome was obtained and designated as the Uz996 strain.

TABLE 2

| Primer | Sequence | SEQ ID NO: |
|---|---|---|
| TB1928 | 5'-TTTGTTTGTTTATGTGTGTTTATTCGAAAC-3' | 74 |
| TB1938 | 5'-TTTGTTTGTTTATGTGTGTTTATTCGAAACTAA GTTCTTGG-3' | 75 |
| TB2236 | 5'-CTTAAGACAGGCCCCTTTTCCTTTG-3' | 76 |
| TB2429 | 5'-CAATGAGGAGTGATTTTACACAAAAAG-3' | 77 |
| TB2654 | 5'-TCGCTCGCAGCCACGGGT-3' | 78 |
| TB2717 | 5'-TAGCGTTGAATGTTAGCGTCAACAAC-3' | 79 |

TABLE 2-continued

| Primer | Sequence | SEQ ID NO: |
|---|---|---|
| TB2799 | 5'-AGGCAAGTGCACAAACAATAC-3' | 80 |
| TB2800 | 5'-ACGACATTACTATATATATAATATAGGAAGCATTTAATAG-3' | 81 |
| TB2859 | 5'-CTGGATAGAGCCTCATCGTTACAC-3' | 82 |
| TB2885 | 5'-AGCCATCGCACTGTACCATG-3' | 83 |
| TB2939 | 5'-CTATGGGACTTCCGGGAAAC-3' | 84 |
| TB2940 | 5'-GAGGGTTGGGCATTCATCAG-3' | 85 |
| TB2943 | 5'-TAACATTCAACGCTATGTGTATTACGATATAGTTAATAGTTGATAG-3' | 86 |
| TB2997 | 5'-ACATAAACAAACAAAATGTCTATCCCAGAAACTCAAAAAG-3' | 87 |
| TB2998 | 5'-AATCACTCCTCATTGTTGTCCTCTGAGGACATAAAATAC-3' | 88 |
| TB3086 | 5'-TTGTCCTCTGAGGACATAAAATACACAC-3' | 89 |
| TB3089 | 5'-ACATAAGAGATCCGCGCGCCTCGTTCAGAATGACAC-3' | 90 |
| TB3090 | 5'-GTCCTCAGAGGACAACGTTTTAAGAGCTTGGTGAG-3' | 91 |
| TB3099 | 5'-CGTGGCTGCGAGCGACGTTTTAAGAGCTTGGTGAG-3' | 92 |
| TB3100 | 5'-GCGGATCTCTTATGTCTTTACGATTTATAGTTTTC-3' | 93 |
| TB3101 | 5'-ATATCGTAATACACACGTTTTAAGAGCTTGGTGAG-3' | 94 |
| TB3102 | 5'-TGTGTATTACGATATAGTTAATAGTTGATAGTTGATTG-3' | 95 |
| TB3172 | 5'-GGGGCCTGTCTTAAGCTTATTTAGAAGTGTCAACAACG-3' | 96 |
| TB3173 | 5'-TAACATTCAACGCTACTGCAGGAATTCGATATC-3' | 97 |
| TB3217 | 5'-ACATAAACAAACAAAGCGAATTTCTTATGATTTATGATTTTTATTATTAAATAAG-3' | 98 |
| TB3326 | 5'-CCAACTGTCCTCACGCTGAC-3' | 99 |
| TB3435 | 5'-TTTGTGCACTTGCCTGCGGATCTCTTATGTCTTTACG-3' | 100 |
| TB3458 | 5'-TGAGGCTCTATCCAGTGACACCGATTATTTAAAGCTG-3' | 101 |
| TB3459 | 5'-TACAGTGCGATGGCTCTTTGCCTTCGTTTATCTTGC-3' | 102 |
| TB3597 | 5'-CCTCATTGCTGCAGGAATTCGATATC-3' | 103 |
| TB3598 | 5'-CCTGCAGCAATGAGGAGTGATTTTACAC-3' | 104 |
| TB4481 | 5'-ATATAGTAATGTCGTTGTGTATTACGATATAGTTAATAGTTGATAGTTG-3' | 105 |

<Fermentation Test in Flask>

With the use of the strains thus prepared, the fermentation test was carried out in a flask in the manner described below. At the outset, 20 ml of YPD liquid medium containing glucose at 20 g/l was introduced into a 100-ml baffled flask, the test strains were inoculated therein, and culture was conducted at 30 degrees C. and 120 rpm for 24 hours. The strains were collected, introduced into a 20-ml flask containing 10 ml of the fermentation medium, and the fermentation test was carried out via shake culture (80 rpm: shake width: 35 mm; 30 degrees C., n=1). The flask was stoppered with a rubber cap comprising a needle (inner diameter: 1.5 mm), and anaerobic conditions of the inside of the flasks was maintained by mounting a check valve at the tip of the needle.

TABLE 3

| Cm200Y10Ac15 15FP | 150 g/l cellulose (Merck), 10 g/l yeast extract, 15 g/l acetic acid, Cellic™ CTec2 (Novozymes) at 15 FPU/g cellulose, pH 6.0 |
|---|---|
| Cm150X60Y10Ac5 25FPU | 150 g/l cellulose (Merck), 60 g/l xylose, 10 g/l yeast extract, 5 g/l acetic acid, Cellic™ CTec2 (Novozymes) at 25 FPU/g cellulose, pH 6.0 |

Glucose, xylose, cellobiose, acetic acid, glycerin, xylitol, and ethanol in the fermentation liquid were measured by HPLC (LC-10A, Shimadzu Seisakusho) under the conditions described below.

Column: AminexHPX-87H;
Mobile phase: $0.01 NH_2SO_4$;
Flow rate: 0.6 ml/min;
Temperature: 30 degrees C.;
Detector: differential refractometer (RID-10A)

<Results of Fermentation Test>

The ADH2-disrupting Uz966 strain (into which no xylose-assimilating gene has been introduced) and the OC2 strain were subjected to the fermentation test in a medium comprising Cm200Y10Ac15FPU, and glucose and acetic acid concentration when ethanol concentration was at the maximal level is shown in Table 4.

TABLE 4

|  | Ethanol (g/l) | Glucose (g/l) | Acetic acid (g/l) |
|---|---|---|---|
| Uz966 strain (Δadh2) | 46.0 | 0.89 | 15.5 |
| OC2 strain | 46.4 | 0.70 | 15.3 |

Duration of fermentation: 89 hours
Amount inoculated: 0.12% PCV

As is apparent from Table 4, no particular difference was observed in terms of fermentation ability between a strain in which the ADH2 gene had been disrupted and a strain in which the ADH2 gene had not been disrupted, when glucose was selectively used as a fermentation substrate.

Subsequently, yeast strains into which xylose-assimilating genes had been introduced were subjected to the fermentation test in a xylose-containing medium (Cm150X60Y10Ac5 25FPU shown in Table 3). The amount inoculated was 0.12% of PCV, and the duration of fermentation was 113 hours. The results are shown in Table 5.

TABLE 5

| Strain | Genotype | Ethanol (g/l) | Xylose (g/l) | Glucose (g/l) | Acetic acid (g/l) |
|---|---|---|---|---|---|
| Uz670 | mhpF | 30.1 | 42.4 | 31.2 | 4.86 |
| Uz669 | mhpF Δadh2 | 33.9 | 41.4 | 27.0 | 4.85 |
| Uz737 | mhpF Δadh2 ADH1 | 51.5 | 36.2 | 10.2 | 4.61 |
| Uz672 | mhpF ADH1 | 33.8 | 40.8 | 28.6 | 4.80 |
| Uz674 | Δadh2 | 19.6 | 53.3 | 32.4 | 5.16 |
| Uz822 | ADH1 | 32.6 | 43.6 | 27.4 | 5.00 |
| Uz644 | Cont. | 33.1 | 38.6 | 24.3 | 4.91 |

As is apparent from Table 5, synergistic effects of improving ethanol conversion and glucose metabolism efficiency were observed in the Uz737 strain in which the mhpF gene and the ADH1 gene are overexpressed and the ADH2 gene is disrupted, compared with the strain overexpressing the acetaldehyde dehydrogenase gene (mhpF). It is also apparent that the Uz737 strain exhibits significantly lowered acetic acid concentration in a medium and improved acetic-acid-assimilating ability. Further, it was found that fermentation of a yeast strain in which ADH2 was disrupted (i.e., the Uz674 strain) would be significantly inhibited in a xylose-containing medium. It was also demonstrated that overexpression of the mhpF gene would enable restoration of fermentative inhibition caused by the destroyed ADH2 gene.

All publications, patents, and patent applications cited herein are incorporated herein by reference in their entirety.

The invention claimed is:

1. A method for producing ethanol comprising a step of culturing a recombinant yeast strain having xylose-metabolizing ability and comprising an acetaldehyde dehydrogenase gene introduced thereinto in a medium containing cellulose, cellulase, and xylose to perform ethanol fermentation, wherein the acetaldehyde dehydrogenase gene encodes the protein (a) or (b) below:

(a) a protein comprising the amino acid sequence as shown in SEQ ID NO: 2; or (b) a protein comprising an amino acid sequence having 90% or higher identity with the amino acid sequence as shown in SEQ ID NO: 2 and having acetaldehyde dehydrogenase activity;

wherein the recombinant yeast strain further comprises a xylose metabolism-associated gene and an alcohol dehydrogenase gene having activity of converting acetaldehyde into ethanol introduced thereinto; and wherein the recombinant yeast strain shows a lowered expression level of an alcohol dehydrogenase gene having activity of converting ethanol into acetaldehyde.

2. The method for producing ethanol according to claim 1, wherein the xylose metabolism-associated gene is the xylose reductase gene, the xylitol dehydrogenase gene, or the xylulokinase gene.

3. The method for producing ethanol according to claim 1, wherein the ethanol fermentation proceeds simultaneously at least with cellulose saccharification.

* * * * *

SEQUENCE LISTING

```
<160> NUMBER OF SEQ ID NOS: 105

<210> SEQ ID NO 1
<211> LENGTH: 951
<212> TYPE: DNA
<213> ORGANISM: Escherichia coli
<220> FEATURE:
<221> NAME/KEY: CDS
<222> LOCATION: (1)..(951)

<400> SEQUENCE: 1 atg tca aag aga aaa gtt gct att atc ggt agt gga aac atc ggt act        48
Met Ser Lys Arg Lys Val Ala Ile Ile Gly Ser Gly Asn Ile Gly Thr
1               5                   10                  15 gat ttg atg atc aag atc ctt aga cat gga caa cac ttg gaa atg gct        96
Asp Leu Met Ile Lys Ile Leu Arg His Gly Gln His Leu Glu Met Ala
                20                  25                  30 gtt atg gtc ggt atc gat cct cag tca gac gga ctt gct aga gcc aga       144
Val Met Val Gly Ile Asp Pro Gln Ser Asp Gly Leu Ala Arg Ala Arg
            35                  40                  45 aga atg ggt gtt gct act aca cat gaa ggt gtt att gga ttg atg aac       192
Arg Met Gly Val Ala Thr Thr His Glu Gly Val Ile Gly Leu Met Asn
        50                  55                  60 atg cca gag ttt gca gat att gac atc gtt ttc gat gct aca agt gca       240
Met Pro Glu Phe Ala Asp Ile Asp Ile Val Phe Asp Ala Thr Ser Ala
65                  70                  75                  80 ggt gct cac gtt aag aat gac gct gcc ttg aga gaa gct aaa cct gat       288
Gly Ala His Val Lys Asn Asp Ala Ala Leu Arg Glu Ala Lys Pro Asp
                85                  90                  95 att aga ttg atc gac ctt acc cca gca gct att gga cca tac tgt gtt       336
Ile Arg Leu Ile Asp Leu Thr Pro Ala Ala Ile Gly Pro Tyr Cys Val
            100                 105                 110 cct gtt gtc aac ttg gag gcc aat gtt gat caa ctt aac gtt aat atg       384
Pro Val Val Asn Leu Glu Ala Asn Val Asp Gln Leu Asn Val Asn Met
        115                 120                 125 gtc aca tgc ggt gga cag gct acc att cct atg gtt gcc gca gtc tct       432
Val Thr Cys Gly Gly Gln Ala Thr Ile Pro Met Val Ala Ala Val Ser
    130                 135                 140 aga gtt gct aga gtc cat tat gcc gaa att atc gca tcc atc gct tca       480
Arg Val Ala Arg Val His Tyr Ala Glu Ile Ile Ala Ser Ile Ala Ser
145                 150                 155                 160 aag agt gca ggt cca gga acc aga gct aac att gac gaa ttc act gag       528
Lys Ser Ala Gly Pro Gly Thr Arg Ala Asn Ile Asp Glu Phe Thr Glu
                165                 170                 175 acc act tct aga gct atc gaa gtt gtc ggt gga gct gcc aag ggt aaa       576
Thr Thr Ser Arg Ala Ile Glu Val Val Gly Gly Ala Ala Lys Gly Lys
            180                 185                 190 gcc att atc gtt ttg aat cct gca gag cca cct ctt atg atg aga gat       624
Ala Ile Ile Val Leu Asn Pro Ala Glu Pro Pro Leu Met Met Arg Asp
        195                 200                 205 act gtt tac gtc ttg tct gac gaa gct tcc caa gat gac att gag gcc       672
Thr Val Tyr Val Leu Ser Asp Glu Ala Ser Gln Asp Asp Ile Glu Ala
```

```
            210                 215                 220
tct atc aac gaa atg gcc gag gca gtt cag gct tac gtc cca ggt tat      720
Ser Ile Asn Glu Met Ala Glu Ala Val Gln Ala Tyr Val Pro Gly Tyr
225                 230                 235                 240 aga ttg aag caa aga gtt cag ttt gag gtc att cca caa gat aaa cct      768
Arg Leu Lys Gln Arg Val Gln Phe Glu Val Ile Pro Gln Asp Lys Pro
                245                 250                 255 gtt aat ttg cca ggt gtc gga cag ttc tcc gga ttg aaa aca gct gtt      816
Val Asn Leu Pro Gly Val Gly Gln Phe Ser Gly Leu Lys Thr Ala Val
            260                 265                 270 tgg ctt gaa gtc gag ggt gca gct cac tac ttg cca gct tat gcc gga      864
Trp Leu Glu Val Glu Gly Ala Ala His Tyr Leu Pro Ala Tyr Ala Gly
        275                 280                 285 aac ctt gac att atg act tct tcc gca ttg gct aca gcc gaa aag atg      912
Asn Leu Asp Ile Met Thr Ser Ser Ala Leu Ala Thr Ala Glu Lys Met
    290                 295                 300 gct caa tct ctt gcc aga aaa gca gga gag gcc gca taa                  951
Ala Gln Ser Leu Ala Arg Lys Ala Gly Glu Ala Ala
305                 310                 315

<210> SEQ ID NO 2
<211> LENGTH: 316
<212> TYPE: PRT
<213> ORGANISM: Escherichia coli

<400> SEQUENCE: 2

Met Ser Lys Arg Lys Val Ala Ile Ile Gly Ser Gly Asn Ile Gly Thr
1               5                   10                  15

Asp Leu Met Ile Lys Ile Leu Arg His Gly Gln His Leu Glu Met Ala
                20                  25                  30

Val Met Val Gly Ile Asp Pro Gln Ser Asp Gly Leu Ala Arg Ala Arg
            35                  40                  45

Arg Met Gly Val Ala Thr Thr His Glu Gly Val Ile Gly Leu Met Asn
        50                  55                  60

Met Pro Glu Phe Ala Asp Ile Asp Ile Val Phe Asp Ala Thr Ser Ala
65                  70                  75                  80

Gly Ala His Val Lys Asn Asp Ala Ala Leu Arg Glu Ala Lys Pro Asp
                85                  90                  95

Ile Arg Leu Ile Asp Leu Thr Pro Ala Ala Ile Gly Pro Tyr Cys Val
            100                 105                 110

Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
    130                 135                 140

Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu
                165                 170                 175

Thr Thr Ser Arg Ala Ile Glu Val Val Gly Gly Ala Ala Lys Gly Lys
            180                 185                 190

Ala Ile Ile Val Leu Asn Pro Ala Glu Pro Pro Leu Met Met Arg Asp
        195                 200                 205

Thr Val Tyr Val Leu Ser Asp Glu Ala Ser Gln Asp Asp Ile Glu Ala
    210                 215                 220

Ser Ile Asn Glu Met Ala Glu Ala Val Gln Ala Tyr Val Pro Gly Tyr
225                 230                 235                 240
```

Arg Leu Lys Gln Arg Val Gln Phe Glu Val Ile Pro Gln Asp Lys Pro
                245                 250                 255

Val Asn Leu Pro Gly Val Gly Gln Phe Ser Gly Leu Lys Thr Ala Val
            260                 265                 270

Trp Leu Glu Val Glu Gly Ala Ala His Tyr Leu Pro Ala Tyr Ala Gly
        275                 280                 285

Asn Leu Asp Ile Met Thr Ser Ser Ala Leu Ala Thr Ala Glu Lys Met
    290                 295                 300

Ala Gln Ser Leu Ala Arg Lys Ala Gly Glu Ala Ala
305                 310                 315

<210> SEQ ID NO 3
<211> LENGTH: 36
<212> TYPE: DNA
<213> ORGANISM: Artificial
<220> FEATURE:
<223> OTHER INFORMATION: Synthetic DNA

<400> SEQUENCE: 3
acccgtggct gcgagcgacc agctaacttg gtcgac                                    36

<210> SEQ ID NO 4
<211> LENGTH: 26
<212> TYPE: DNA
<213> ORGANISM: Artificial
<220> FEATURE:
<223> OTHER INFORMATION: Synthetic DNA

<400> SEQUENCE: 4
cctcattgct ggatagagcc tcatcg                                               26

<210> SEQ ID NO 5
<211> LENGTH: 30
<212> TYPE: DNA
<213> ORGANISM: Artificial
<220> FEATURE:
<223> OTHER INFORMATION: Synthetic DNA

<400> SEQUENCE: 5
tctatccagc aatgaggagt gattttacac                                           30

<210> SEQ ID NO 6
<211> LENGTH: 33
<212> TYPE: DNA
<213> ORGANISM: Artificial
<220> FEATURE:
<223> OTHER INFORMATION: Synthetic DNA

<400> SEQUENCE: 6
gagcaacaca gtttatctta tatgtattca atg                                       33

<210> SEQ ID NO 7
<211> LENGTH: 37
<212> TYPE: DNA
<213> ORGANISM: Artificial
<220> FEATURE:
<223> OTHER INFORMATION: Synthetic DNA

<400> SEQUENCE: 7
ttttattatt agtcttttttt tttttgaca atatctg                                   37

<210> SEQ ID NO 8
<211> LENGTH: 18
<212> TYPE: DNA

```
<213> ORGANISM: Artificial
<220> FEATURE:
<223> OTHER INFORMATION: Synthetic DNA

<400> SEQUENCE: 8
tcgctcgcag ccacgggt                                                    18

<210> SEQ ID NO 9
<211> LENGTH: 33
<212> TYPE: DNA
<213> ORGANISM: Artificial
<220> FEATURE:
<223> OTHER INFORMATION: Synthetic DNA

<400> SEQUENCE: 9
taaactgtgt tgctcttatg cggcctctcc tgc                                   33

<210> SEQ ID NO 10
<211> LENGTH: 43
<212> TYPE: DNA
<213> ORGANISM: Artificial
<220> FEATURE:
<223> OTHER INFORMATION: Synthetic DNA

<400> SEQUENCE: 10
agactaataa taaaaatgtc aaagagaaaa gttgctatta tcg                        43

<210> SEQ ID NO 11
<211> LENGTH: 20
<212> TYPE: DNA
<213> ORGANISM: Artificial
<220> FEATURE:
<223> OTHER INFORMATION: Synthetic DNA

<400> SEQUENCE: 11
gttgaagtcg cctggtagcc                                                  20

<210> SEQ ID NO 12
<211> LENGTH: 20
<212> TYPE: DNA
<213> ORGANISM: Artificial
<220> FEATURE:
<223> OTHER INFORMATION: Synthetic DNA

<400> SEQUENCE: 12
cggtgatccc cttgaaaaag                                                  20

<210> SEQ ID NO 13
<211> LENGTH: 20
<212> TYPE: DNA
<213> ORGANISM: Artificial
<220> FEATURE:
<223> OTHER INFORMATION: Synthetic DNA

<400> SEQUENCE: 13
tccctccacc aaaggtgttc                                                  20

<210> SEQ ID NO 14
<211> LENGTH: 22
<212> TYPE: DNA
<213> ORGANISM: Artificial
<220> FEATURE:
<223> OTHER INFORMATION: Synthetic DNA

<400> SEQUENCE: 14
ttgcaaagaa ccgtcaccaa tg                                               22
```

<210> SEQ ID NO 15
<211> LENGTH: 20
<212> TYPE: DNA
<213> ORGANISM: Artificial
<220> FEATURE:
<223> OTHER INFORMATION: Synthetic DNA

<400> SEQUENCE: 15
gttgaagtcg cctggtagcc                                        20

<210> SEQ ID NO 16
<211> LENGTH: 20
<212> TYPE: DNA
<213> ORGANISM: Artificial
<220> FEATURE:
<223> OTHER INFORMATION: Synthetic DNA

<400> SEQUENCE: 16
cggtgatccc cttgaaaaag                                        20

<210> SEQ ID NO 17
<211> LENGTH: 16
<212> TYPE: DNA
<213> ORGANISM: Artificial
<220> FEATURE:
<223> OTHER INFORMATION: Synthetic DNA

<400> SEQUENCE: 17
tgcggccggc cgcagc                                            16

<210> SEQ ID NO 18
<211> LENGTH: 34
<212> TYPE: DNA
<213> ORGANISM: Artificial
<220> FEATURE:
<223> OTHER INFORMATION: Synthetic DNA

<400> SEQUENCE: 18
cgctaacatt caacgctaag agcgcgcctc gttc                        34

<210> SEQ ID NO 19
<211> LENGTH: 26
<212> TYPE: DNA
<213> ORGANISM: Artificial
<220> FEATURE:
<223> OTHER INFORMATION: Synthetic DNA

<400> SEQUENCE: 19
tagcgttgaa tgttagcgtc aacaac                                 26

<210> SEQ ID NO 20
<211> LENGTH: 30
<212> TYPE: DNA
<213> ORGANISM: Artificial
<220> FEATURE:
<223> OTHER INFORMATION: Synthetic DNA

<400> SEQUENCE: 20
tttgtttgtt tatgtgtgtt tattcgaaac                             30

<210> SEQ ID NO 21
<211> LENGTH: 37
<212> TYPE: DNA
<213> ORGANISM: Artificial
<220> FEATURE:

<223> OTHER INFORMATION: Synthetic DNA

<400> SEQUENCE: 21
tgcatgtcta ctaaactcac aaattagagc ttcaatt                                37

<210> SEQ ID NO 22
<211> LENGTH: 41
<212> TYPE: DNA
<213> ORGANISM: Artificial
<220> FEATURE:
<223> OTHER INFORMATION: Synthetic DNA

<400> SEQUENCE: 22
gtcgaccaag ttagctgggg gtaataactg atataattaa a                           41

<210> SEQ ID NO 23
<211> LENGTH: 21
<212> TYPE: DNA
<213> ORGANISM: Artificial
<220> FEATURE:
<223> OTHER INFORMATION: Synthetic DNA

<400> SEQUENCE: 23
ccagctaact tggtcgactt g                                                 21

<210> SEQ ID NO 24
<211> LENGTH: 22
<212> TYPE: DNA
<213> ORGANISM: Artificial
<220> FEATURE:
<223> OTHER INFORMATION: Synthetic DNA

<400> SEQUENCE: 24
ttgcaaagaa ccgtcaccaa tg                                                22

<210> SEQ ID NO 25
<211> LENGTH: 33
<212> TYPE: DNA
<213> ORGANISM: Artificial
<220> FEATURE:
<223> OTHER INFORMATION: Synthetic DNA

<400> SEQUENCE: 25
acataaacaa acaaaatgac cgaccaagcg acg                                    33

<210> SEQ ID NO 26
<211> LENGTH: 35
<212> TYPE: DNA
<213> ORGANISM: Artificial
<220> FEATURE:
<223> OTHER INFORMATION: Synthetic DNA

<400> SEQUENCE: 26
agtttagtag acatgcatca tgagatgcct gcaag                                  35

<210> SEQ ID NO 27
<211> LENGTH: 36
<212> TYPE: DNA
<213> ORGANISM: Artificial
<220> FEATURE:
<223> OTHER INFORMATION: Synthetic DNA

<400> SEQUENCE: 27
ctgcggccgg ccgcacttcc aagcatctca taaacc                                 36

<210> SEQ ID NO 28
<211> LENGTH: 34
<212> TYPE: DNA
<213> ORGANISM: Artificial
<220> FEATURE:
<223> OTHER INFORMATION: Synthetic DNA

<400> SEQUENCE: 28
acataaacaa acaaagatgt acgatcgcct gcac        34

<210> SEQ ID NO 29
<211> LENGTH: 30
<212> TYPE: DNA
<213> ORGANISM: Artificial
<220> FEATURE:
<223> OTHER INFORMATION: Synthetic DNA

<400> SEQUENCE: 29
tttgtttgtt tatgtgtgtt tattcgaaac        30

<210> SEQ ID NO 30
<211> LENGTH: 34
<212> TYPE: DNA
<213> ORGANISM: Artificial
<220> FEATURE:
<223> OTHER INFORMATION: Synthetic DNA

<400> SEQUENCE: 30
gacggttctt tgcaagatgt acgatcgcct gcac        34

<210> SEQ ID NO 31
<211> LENGTH: 25
<212> TYPE: DNA
<213> ORGANISM: Artificial
<220> FEATURE:
<223> OTHER INFORMATION: Synthetic DNA

<400> SEQUENCE: 31
tgcggccggc cgcagctttg cagag        25

<210> SEQ ID NO 32
<211> LENGTH: 26
<212> TYPE: DNA
<213> ORGANISM: Artificial
<220> FEATURE:
<223> OTHER INFORMATION: Synthetic DNA

<400> SEQUENCE: 32
cttgacgggt attctgagca tcttac        26

<210> SEQ ID NO 33
<211> LENGTH: 35
<212> TYPE: DNA
<213> ORGANISM: Artificial
<220> FEATURE:
<223> OTHER INFORMATION: Synthetic DNA

<400> SEQUENCE: 33
tttgttttgt tgtttgtgt gatgaattta atttg        35

<210> SEQ ID NO 34
<211> LENGTH: 35
<212> TYPE: DNA
<213> ORGANISM: Artificial
<220> FEATURE:
<223> OTHER INFORMATION: Synthetic DNA

<400> SEQUENCE: 34
aacaaacaaa acaaaatgct ttcactacgt caatc        35

<210> SEQ ID NO 35
<211> LENGTH: 41
<212> TYPE: DNA
<213> ORGANISM: Artificial
<220> FEATURE:
<223> OTHER INFORMATION: Synthetic DNA

<400> SEQUENCE: 35 cttaatctttt gtcataagag catatctaga gctacacaaa g        41

<210> SEQ ID NO 36
<211> LENGTH: 27
<212> TYPE: DNA
<213> ORGANISM: Artificial
<220> FEATURE:
<223> OTHER INFORMATION: Synthetic DNA

<400> SEQUENCE: 36
atgacaaaga ttaaggtagc taacccc        27

<210> SEQ ID NO 37
<211> LENGTH: 35
<212> TYPE: DNA
<213> ORGANISM: Artificial
<220> FEATURE:
<223> OTHER INFORMATION: Synthetic DNA

<400> SEQUENCE: 37
gaccaagtta gctggtatat cggtcctctg tgtag        35

<210> SEQ ID NO 38
<211> LENGTH: 38
<212> TYPE: DNA
<213> ORGANISM: Artificial
<220> FEATURE:
<223> OTHER INFORMATION: Synthetic DNA

<400> SEQUENCE: 38
acataaacaa acaaaatggc aaacccttttt tcgagatg        38

<210> SEQ ID NO 39
<211> LENGTH: 37
<212> TYPE: DNA
<213> ORGANISM: Artificial
<220> FEATURE:
<223> OTHER INFORMATION: Synthetic DNA

<400> SEQUENCE: 39
agaatacccg tcaagctgga tagagcctca tcgttac        37

<210> SEQ ID NO 40
<211> LENGTH: 21
<212> TYPE: DNA
<213> ORGANISM: Artificial
<220> FEATURE:
<223> OTHER INFORMATION: Synthetic DNA

<400> SEQUENCE: 40
tgggaatatt accgctcgaa g        21

<210> SEQ ID NO 41
<211> LENGTH: 20

```
<212> TYPE: DNA
<213> ORGANISM: Artificial
<220> FEATURE:
<223> OTHER INFORMATION: Synthetic DNA

<400> SEQUENCE: 41 aaggggggaag gtgtggaatc                                              20

<210> SEQ ID NO 42
<211> LENGTH: 33
<212> TYPE: DNA
<213> ORGANISM: Artificial
<220> FEATURE:
<223> OTHER INFORMATION: Synthetic DNA

<400> SEQUENCE: 42
cacaccttcc cccttgatcc tctagagtcg acc                                33

<210> SEQ ID NO 43
<211> LENGTH: 35
<212> TYPE: DNA
<213> ORGANISM: Artificial
<220> FEATURE:
<223> OTHER INFORMATION: Synthetic DNA

<400> SEQUENCE: 43
gcggtaatat tcccagatcc ccgggtaccg agctc                              35

<210> SEQ ID NO 44
<211> LENGTH: 33
<212> TYPE: DNA
<213> ORGANISM: Artificial
<220> FEATURE:
<223> OTHER INFORMATION: Synthetic DNA

<400> SEQUENCE: 44
aacgaggcgc gctcttccag ccagtaaaat cca                                33

<210> SEQ ID NO 45
<211> LENGTH: 44
<212> TYPE: DNA
<213> ORGANISM: Artificial
<220> FEATURE:
<223> OTHER INFORMATION: Synthetic DNA

<400> SEQUENCE: 45
gctatggtgt gtgggcttta aaaatttcc aattttcctt tacg                     44

<210> SEQ ID NO 46
<211> LENGTH: 24
<212> TYPE: DNA
<213> ORGANISM: Artificial
<220> FEATURE:
<223> OTHER INFORMATION: Synthetic DNA

<400> SEQUENCE: 46
cccacacacc atagcttcaa aatg                                          24

<210> SEQ ID NO 47
<211> LENGTH: 41
<212> TYPE: DNA
<213> ORGANISM: Artificial
<220> FEATURE:
<223> OTHER INFORMATION: Synthetic DNA

<400> SEQUENCE: 47
```

```
tctttagatt agattgctat gctttctttc taatgagcaa g                    41

<210> SEQ ID NO 48
<211> LENGTH: 40
<212> TYPE: DNA
<213> ORGANISM: Artificial
<220> FEATURE:
<223> OTHER INFORMATION: Synthetic DNA

<400> SEQUENCE: 48
aatctaatct aaagaatgtt gtgttcagta attcagagac                      40

<210> SEQ ID NO 49
<211> LENGTH: 39
<212> TYPE: DNA
<213> ORGANISM: Artificial
<220> FEATURE:
<223> OTHER INFORMATION: Synthetic DNA

<400> SEQUENCE: 49
ctgcggccgg ccgcattaga tgagagtctt ttccagttc                       39

<210> SEQ ID NO 50
<211> LENGTH: 16
<212> TYPE: DNA
<213> ORGANISM: Artificial
<220> FEATURE:
<223> OTHER INFORMATION: Synthetic DNA

<400> SEQUENCE: 50
tgcggccggc cgcagc                                                16

<210> SEQ ID NO 51
<211> LENGTH: 18
<212> TYPE: DNA
<213> ORGANISM: Artificial
<220> FEATURE:
<223> OTHER INFORMATION: Synthetic DNA

<400> SEQUENCE: 51
gcgcctcgtt cagaatga                                              18

<210> SEQ ID NO 52
<211> LENGTH: 21
<212> TYPE: DNA
<213> ORGANISM: Artificial
<220> FEATURE:
<223> OTHER INFORMATION: Synthetic DNA

<400> SEQUENCE: 52
tccagccagt aaaatccata c                                          21

<210> SEQ ID NO 53
<211> LENGTH: 26
<212> TYPE: DNA
<213> ORGANISM: Artificial
<220> FEATURE:
<223> OTHER INFORMATION: Synthetic DNA

<400> SEQUENCE: 53
ccgtcaagag agcgcgcctc gttcag                                     26

<210> SEQ ID NO 54
<211> LENGTH: 33
<212> TYPE: DNA
<213> ORGANISM: Artificial
```

<220> FEATURE:
<223> OTHER INFORMATION: Synthetic DNA

<400> SEQUENCE: 54
gcgctctctt gacgggtatt ctgagcatct tac                          33

<210> SEQ ID NO 55
<211> LENGTH: 35
<212> TYPE: DNA
<213> ORGANISM: Artificial
<220> FEATURE:
<223> OTHER INFORMATION: Synthetic DNA

<400> SEQUENCE: 55
tttgttttgt tgtttgtgt gatgaattta atttg                         35

<210> SEQ ID NO 56
<211> LENGTH: 36
<212> TYPE: DNA
<213> ORGANISM: Artificial
<220> FEATURE:
<223> OTHER INFORMATION: Synthetic DNA

<400> SEQUENCE: 56
aacaaacaaa acaaaatgcc ttctattaag ttgaac                       36

<210> SEQ ID NO 57
<211> LENGTH: 37
<212> TYPE: DNA
<213> ORGANISM: Artificial
<220> FEATURE:
<223> OTHER INFORMATION: Synthetic DNA

<400> SEQUENCE: 57
ggggcctata atgcattaga cgaagatagg aatcttg                      37

<210> SEQ ID NO 58
<211> LENGTH: 36
<212> TYPE: DNA
<213> ORGANISM: Artificial
<220> FEATURE:
<223> OTHER INFORMATION: Synthetic DNA

<400> SEQUENCE: 58
aacaaacaaa acaaaatgcc ttctattaag ttgaac                       36

<210> SEQ ID NO 59
<211> LENGTH: 41
<212> TYPE: DNA
<213> ORGANISM: Artificial
<220> FEATURE:
<223> OTHER INFORMATION: Synthetic DNA

<400> SEQUENCE: 59
attttactgg ctggaatttc gtagattata attaaggcga c                 41

<210> SEQ ID NO 60
<211> LENGTH: 45
<212> TYPE: DNA
<213> ORGANISM: Artificial
<220> FEATURE:
<223> OTHER INFORMATION: Synthetic DNA

<400> SEQUENCE: 60
agttgcttga cacggtggaa gaaggtccag ccagtaaaat ccata             45

<210> SEQ ID NO 61
<211> LENGTH: 26
<212> TYPE: DNA
<213> ORGANISM: Artificial
<220> FEATURE:
<223> OTHER INFORMATION: Synthetic DNA

<400> SEQUENCE: 61
atttcgtaga ttataattaa ggcgac                                    26

<210> SEQ ID NO 62
<211> LENGTH: 28
<212> TYPE: DNA
<213> ORGANISM: Artificial
<220> FEATURE:
<223> OTHER INFORMATION: Synthetic DNA

<400> SEQUENCE: 62
tttgattgat ttgactgtgt tattttgc                                  28

<210> SEQ ID NO 63
<211> LENGTH: 20
<212> TYPE: DNA
<213> ORGANISM: Artificial
<220> FEATURE:
<223> OTHER INFORMATION: Synthetic DNA

<400> SEQUENCE: 63
ccgtgtcaag caactatggg                                           20

<210> SEQ ID NO 64
<211> LENGTH: 35
<212> TYPE: DNA
<213> ORGANISM: Artificial
<220> FEATURE:
<223> OTHER INFORMATION: Synthetic DNA

<400> SEQUENCE: 64
tataatctac gaaattaata agaaaggtga ccgtg                          35

<210> SEQ ID NO 65
<211> LENGTH: 20
<212> TYPE: DNA
<213> ORGANISM: Artificial
<220> FEATURE:
<223> OTHER INFORMATION: Synthetic DNA

<400> SEQUENCE: 65
gttagtctct cggccttgcg                                           20

<210> SEQ ID NO 66
<211> LENGTH: 33
<212> TYPE: DNA
<213> ORGANISM: Artificial
<220> FEATURE:
<223> OTHER INFORMATION: Synthetic DNA

<400> SEQUENCE: 66
ggccgagaga ctaacttact cagggccgtc aat                            33

<210> SEQ ID NO 67
<211> LENGTH: 33
<212> TYPE: DNA
<213> ORGANISM: Artificial
<220> FEATURE:
<223> OTHER INFORMATION: Synthetic DNA

<400> SEQUENCE: 67
gtcaaatcaa tcaaaatgac tgctaaccct tcc                          33

<210> SEQ ID NO 68
<211> LENGTH: 20
<212> TYPE: DNA
<213> ORGANISM: Artificial
<220> FEATURE:
<223> OTHER INFORMATION: Synthetic DNA

<400> SEQUENCE: 68
tggggctaaa cgagatttgg                                         20

<210> SEQ ID NO 69
<211> LENGTH: 24
<212> TYPE: DNA
<213> ORGANISM: Artificial
<220> FEATURE:
<223> OTHER INFORMATION: Synthetic DNA

<400> SEQUENCE: 69
gaaatttagt atgctgtgct tggg                                    24

<210> SEQ ID NO 70
<211> LENGTH: 1047
<212> TYPE: DNA
<213> ORGANISM: Saccharomyces cerevisiae
<220> FEATURE:
<221> NAME/KEY: CDS
<222> LOCATION: (1)..(1047)

<400> SEQUENCE: 70

```
atg tct atc cca gaa act caa aaa ggt gtt atc ttc tac gaa tcc cac      48
Met Ser Ile Pro Glu Thr Gln Lys Gly Val Ile Phe Tyr Glu Ser His
1               5                  10                  15 ggt aag ttg gaa tac aaa gat att cca gtt cca aag cca aag gcc aac      96
Gly Lys Leu Glu Tyr Lys Asp Ile Pro Val Pro Lys Pro Lys Ala Asn
            20                  25                  30 gaa ttg ttg atc aac gtt aaa tac tct ggt gtc tgt cac act gac ttg     144
Glu Leu Leu Ile Asn Val Lys Tyr Ser Gly Val Cys His Thr Asp Leu
        35                  40                  45 cac gct tgg cac ggt gac tgg cca ttg cca gtt aag cta cca tta gtc     192
His Ala Trp His Gly Asp Trp Pro Leu Pro Val Lys Leu Pro Leu Val
    50                  55                  60 ggt ggt cac gaa ggt gcc ggt gtc gtt gtc ggc atg ggt gaa aac gtt     240
Gly Gly His Glu Gly Ala Gly Val Val Val Gly Met Gly Glu Asn Val
65                  70                  75                  80 aag ggc tgg aag atc ggt gac tac gcc ggt atc aaa tgg ttg aac ggt     288
Lys Gly Trp Lys Ile Gly Asp Tyr Ala Gly Ile Lys Trp Leu Asn Gly
                85                  90                  95 tct tgt atg gcc tgt gaa tac tgt gaa ttg ggt aac gaa tcc aac tgt     336
Ser Cys Met Ala Cys Glu Tyr Cys Glu Leu Gly Asn Glu Ser Asn Cys
            100                 105                 110 cct cac gct gac ttg tct ggt tac acc cac gac ggt tct ttc caa caa     384
Pro His Ala Asp Leu Ser Gly Tyr Thr His Asp Gly Ser Phe Gln Gln
        115                 120                 125 tac gct acc gct gac gct gtt caa gcc gct cac att cct caa ggt acc     432
Tyr Ala Thr Ala Asp Ala Val Gln Ala Ala His Ile Pro Gln Gly Thr
    130                 135                 140 gac ttg gcc caa gtc gcc ccc atc ttg tgt gct ggt atc acc gtc tac     480
Asp Leu Ala Gln Val Ala Pro Ile Leu Cys Ala Gly Ile Thr Val Tyr
145                 150                 155                 160
```

| | | | | | | | | | | | | | | | | |
|---|---|---|---|---|---|---|---|---|---|---|---|---|---|---|---|---|
| aag | gct | ttg | aag | tct | gct | aac | ttg | atg | gcc | ggt | cac | tgg | gtt | gct | atc | 528 |
| Lys | Ala | Leu | Lys | Ser | Ala | Asn | Leu | Met | Ala | Gly | His | Trp | Val | Ala | Ile | |
| | | | 165 | | | | | 170 | | | | | | 175 | | |
| tcc | ggt | gct | gct | ggt | ggt | cta | ggt | tct | ttg | gct | gtt | caa | tac | gcc | aag | 576 |
| Ser | Gly | Ala | Ala | Gly | Gly | Leu | Gly | Ser | Leu | Ala | Val | Gln | Tyr | Ala | Lys | |
| | | 180 | | | | | | 185 | | | | | 190 | | | |
| gct | atg | ggt | tac | aga | gtc | ttg | ggt | att | gac | ggt | ggt | gaa | ggt | aag | gaa | 624 |
| Ala | Met | Gly | Tyr | Arg | Val | Leu | Gly | Ile | Asp | Gly | Gly | Glu | Gly | Lys | Glu | |
| | | 195 | | | | | 200 | | | | | 205 | | | | |
| gaa | tta | ttc | aga | tcc | atc | ggt | ggt | gaa | gtc | ttc | att | gac | ttc | act | aag | 672 |
| Glu | Leu | Phe | Arg | Ser | Ile | Gly | Gly | Glu | Val | Phe | Ile | Asp | Phe | Thr | Lys | |
| | 210 | | | | | 215 | | | | | 220 | | | | | |
| gaa | aag | gac | att | gtc | ggt | gct | gtt | cta | aag | gcc | act | gac | ggt | ggt | gct | 720 |
| Glu | Lys | Asp | Ile | Val | Gly | Ala | Val | Leu | Lys | Ala | Thr | Asp | Gly | Gly | Ala | |
| 225 | | | | | 230 | | | | | 235 | | | | | 240 | |
| cac | ggt | gtc | atc | aac | gtt | tcc | gtt | tcc | gaa | gcc | gct | att | gaa | gct | tct | 768 |
| His | Gly | Val | Ile | Asn | Val | Ser | Val | Ser | Glu | Ala | Ala | Ile | Glu | Ala | Ser | |
| | | | | 245 | | | | | 250 | | | | | 255 | | |
| acc | aga | tac | gtt | aga | gct | aac | ggt | acc | acc | gtt | ttg | gtc | ggt | atg | cca | 816 |
| Thr | Arg | Tyr | Val | Arg | Ala | Asn | Gly | Thr | Thr | Val | Leu | Val | Gly | Met | Pro | |
| | | | 260 | | | | | 265 | | | | | 270 | | | |
| gct | ggt | gcc | aag | tgt | tgt | tct | gat | gtc | ttc | aac | caa | gtc | gtc | aag | tcc | 864 |
| Ala | Gly | Ala | Lys | Cys | Cys | Ser | Asp | Val | Phe | Asn | Gln | Val | Val | Lys | Ser | |
| | | 275 | | | | | 280 | | | | | 285 | | | | |
| atc | tct | att | gtt | ggt | tct | tac | gtc | ggt | aac | aga | gct | gac | acc | aga | gaa | 912 |
| Ile | Ser | Ile | Val | Gly | Ser | Tyr | Val | Gly | Asn | Arg | Ala | Asp | Thr | Arg | Glu | |
| | | 290 | | | | | 295 | | | | | 300 | | | | |
| gct | ttg | gac | ttc | ttc | gcc | aga | ggt | ttg | gtc | aag | tct | cca | atc | aag | gtt | 960 |
| Ala | Leu | Asp | Phe | Phe | Ala | Arg | Gly | Leu | Val | Lys | Ser | Pro | Ile | Lys | Val | |
| 305 | | | | | 310 | | | | | 315 | | | | | 320 | |
| gtc | ggc | ttg | tct | acc | ttg | cca | gaa | att | tac | gaa | aag | atg | gaa | aag | ggt | 1008 |
| Val | Gly | Leu | Ser | Thr | Leu | Pro | Glu | Ile | Tyr | Glu | Lys | Met | Glu | Lys | Gly | |
| | | | | 325 | | | | | 330 | | | | | 335 | | |
| caa | atc | gtt | ggt | aga | tac | gtt | gtt | gac | act | tct | aaa | taa | | | | 1047 |
| Gln | Ile | Val | Gly | Arg | Tyr | Val | Val | Asp | Thr | Ser | Lys | | | | | |
| | | | 340 | | | | | 345 | | | | | | | | |

<210> SEQ ID NO 71
<211> LENGTH: 348
<212> TYPE: PRT
<213> ORGANISM: Saccharomyces cerevisiae

<400> SEQUENCE: 71

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln

```
                    115                 120                 125
Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345

<210> SEQ ID NO 72
<211> LENGTH: 1047
<212> TYPE: DNA
<213> ORGANISM: Saccharomyces cerevisiae
<220> FEATURE:
<221> NAME/KEY: CDS
<222> LOCATION: (1)..(1047)

<400> SEQUENCE: 72 atg tct att cca gaa act caa aaa gcc att atc ttc tac gaa tcc aac     48
Met Ser Ile Pro Glu Thr Gln Lys Ala Ile Ile Phe Tyr Glu Ser Asn
1               5                   10                  15 ggc aag ttg gag cat aag gat atc cca gtt cca aag cca aag ccc aac     96
Gly Lys Leu Glu His Lys Asp Ile Pro Val Pro Lys Pro Lys Pro Asn
            20                  25                  30 gaa ttg tta atc aac gtc aag tac tct ggt gtc tgc cac acc gat ttg    144
Glu Leu Leu Ile Asn Val Lys Tyr Ser Gly Val Cys His Thr Asp Leu
        35                  40                  45 cac gct tgg cat ggt gac tgg cca ttg cca act aag tta cca tta gtt    192
His Ala Trp His Gly Asp Trp Pro Leu Pro Thr Lys Leu Pro Leu Val
    50                  55                  60 ggt ggt cac gaa ggt gcc ggt gtc gtt gtc ggc atg ggt gaa aac gtt    240
Gly Gly His Glu Gly Ala Gly Val Val Val Gly Met Gly Glu Asn Val
65                  70                  75                  80 aag ggc tgg aag atc ggt gac tac gcc ggt atc aaa tgg ttg aac ggt    288
Lys Gly Trp Lys Ile Gly Asp Tyr Ala Gly Ile Lys Trp Leu Asn Gly
                85                  90                  95
```

| | | | | | | | | | | | | | | | | |
|---|---|---|---|---|---|---|---|---|---|---|---|---|---|---|---|---|
| tct | tgt | atg | gcc | tgt | gaa | tac | tgt | gaa | ttg | ggt | aac | gaa | tcc | aac | tgt | 336 |
| Ser | Cys | Met | Ala | Cys | Glu | Tyr | Cys | Glu | Leu | Gly | Asn | Glu | Ser | Asn | Cys | |
| | | | 100 | | | | | 105 | | | | | 110 | | | |
| cct | cac | gct | gac | ttg | tct | ggt | tac | acc | cac | gac | ggt | tct | ttc | caa | gaa | 384 |
| Pro | His | Ala | Asp | Leu | Ser | Gly | Tyr | Thr | His | Asp | Gly | Ser | Phe | Gln | Glu | |
| | | 115 | | | | | 120 | | | | | 125 | | | | |
| tac | gct | acc | gct | gac | gct | gtt | caa | gcc | gct | cac | att | cct | caa | ggt | act | 432 |
| Tyr | Ala | Thr | Ala | Asp | Ala | Val | Gln | Ala | Ala | His | Ile | Pro | Gln | Gly | Thr | |
| 130 | | | | | 135 | | | | | 140 | | | | | | |
| gac | ttg | gct | gaa | gtc | gcg | cca | atc | ttg | tgt | gct | ggt | atc | acc | gta | tac | 480 |
| Asp | Leu | Ala | Glu | Val | Ala | Pro | Ile | Leu | Cys | Ala | Gly | Ile | Thr | Val | Tyr | |
| 145 | | | | 150 | | | | | 155 | | | | | 160 | | |
| aag | gct | ttg | aag | tct | gcc | aac | ttg | aga | gca | ggc | cac | tgg | gcg | gcc | att | 528 |
| Lys | Ala | Leu | Lys | Ser | Ala | Asn | Leu | Arg | Ala | Gly | His | Trp | Ala | Ala | Ile | |
| | | | 165 | | | | | 170 | | | | | 175 | | | |
| tct | ggt | gct | gct | ggt | ggt | cta | ggt | tct | ttg | gct | gtt | caa | tat | gct | aag | 576 |
| Ser | Gly | Ala | Ala | Gly | Gly | Leu | Gly | Ser | Leu | Ala | Val | Gln | Tyr | Ala | Lys | |
| | | 180 | | | | | 185 | | | | | 190 | | | | |
| gcg | atg | ggt | tac | aga | gtc | tta | ggt | att | gat | ggt | ggt | cca | gga | aag | gaa | 624 |
| Ala | Met | Gly | Tyr | Arg | Val | Leu | Gly | Ile | Asp | Gly | Gly | Pro | Gly | Lys | Glu | |
| 195 | | | | | 200 | | | | | 205 | | | | | | |
| gaa | ttg | ttt | acc | tcg | ctc | ggt | ggt | gaa | gta | ttc | atc | gac | ttc | acc | aaa | 672 |
| Glu | Leu | Phe | Thr | Ser | Leu | Gly | Gly | Glu | Val | Phe | Ile | Asp | Phe | Thr | Lys | |
| | 210 | | | | | 215 | | | | | 220 | | | | | |
| gag | aag | gac | att | gtt | agc | gca | gtc | gtt | aag | gct | acc | aac | ggc | ggt | gcc | 720 |
| Glu | Lys | Asp | Ile | Val | Ser | Ala | Val | Val | Lys | Ala | Thr | Asn | Gly | Gly | Ala | |
| 225 | | | | | 230 | | | | | 235 | | | | | 240 | |
| cac | ggt | atc | atc | aat | gtt | tcc | gtt | tcc | gaa | gcc | gct | atc | gaa | gct | tct | 768 |
| His | Gly | Ile | Ile | Asn | Val | Ser | Val | Ser | Glu | Ala | Ala | Ile | Glu | Ala | Ser | |
| | | | 245 | | | | | 250 | | | | | 255 | | | |
| acc | aga | tac | tgt | agg | gcg | aac | ggt | act | gtt | gtc | ttg | gtt | ggt | ttg | cca | 816 |
| Thr | Arg | Tyr | Cys | Arg | Ala | Asn | Gly | Thr | Val | Val | Leu | Val | Gly | Leu | Pro | |
| | | 260 | | | | | 265 | | | | | 270 | | | | |
| gcc | ggt | gca | aag | tgc | tcc | tct | gat | gtc | ttc | aac | cac | gtt | gtc | aag | tct | 864 |
| Ala | Gly | Ala | Lys | Cys | Ser | Ser | Asp | Val | Phe | Asn | His | Val | Val | Lys | Ser | |
| 275 | | | | | 280 | | | | | 285 | | | | | | |
| atc | tcc | att | gtc | ggc | tct | tac | gtg | ggg | aac | aga | gct | gat | acc | aga | gaa | 912 |
| Ile | Ser | Ile | Val | Gly | Ser | Tyr | Val | Gly | Asn | Arg | Ala | Asp | Thr | Arg | Glu | |
| | 290 | | | | | 295 | | | | | 300 | | | | | |
| gcc | tta | gat | ttc | ttt | gcc | aga | ggt | cta | gtc | aag | tct | cca | ata | aag | gta | 960 |
| Ala | Leu | Asp | Phe | Phe | Ala | Arg | Gly | Leu | Val | Lys | Ser | Pro | Ile | Lys | Val | |
| 305 | | | | 310 | | | | | 315 | | | | | 320 | | |
| gtt | ggc | tta | tcc | agt | tta | cca | gaa | att | tac | gaa | aag | atg | gag | aag | ggc | 1008 |
| Val | Gly | Leu | Ser | Ser | Leu | Pro | Glu | Ile | Tyr | Glu | Lys | Met | Glu | Lys | Gly | |
| | | | 325 | | | | | 330 | | | | | 335 | | | |
| caa | att | gct | ggt | aga | tac | gtt | gtt | gac | act | tct | aaa | taa | | | | 1047 |
| Gln | Ile | Ala | Gly | Arg | Tyr | Val | Val | Asp | Thr | Ser | Lys | | | | | |
| | | 340 | | | | | 345 | | | | | | | | | |

<210> SEQ ID NO 73
<211> LENGTH: 348
<212> TYPE: PRT
<213> ORGANISM: Saccharomyces cerevisiae

<400> SEQUENCE: 73

Met Ser Ile Pro Glu Thr Gln Lys Ala Ile Ile Phe Tyr Glu Ser Asn
1               5                   10                  15

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu

```
                35                  40                  45
His Ala Trp His Gly Asp Trp Pro Leu Pro Thr Lys Leu Pro Leu Val
 50                  55                  60
Gly Gly His Glu Gly Ala Gly Val Val Val Gly Met Gly Glu Asn Val
 65                  70                  75                  80
Lys Gly Trp Lys Ile Gly Asp Tyr Ala Gly Ile Lys Trp Leu Asn Gly
                 85                  90                  95
Ser Cys Met Ala Cys Glu Tyr Cys Leu Gly Asn Glu Ser Asn Cys
                100                 105                 110
Pro His Ala Asp Leu Ser Gly Tyr Thr His Asp Gly Ser Phe Gln Glu
                115                 120                 125
Tyr Ala Thr Ala Asp Ala Val Gln Ala Ala His Ile Pro Gln Gly Thr
130                 135                 140
Asp Leu Ala Glu Val Ala Pro Ile Leu Cys Ala Gly Ile Thr Val Tyr
145                 150                 155                 160
Lys Ala Leu Lys Ser Ala Asn Leu Arg Ala Gly His Trp Ala Ala Ile
                165                 170                 175
Ser Gly Ala Ala Gly Gly Leu Gly Ser Leu Ala Val Gln Tyr Ala Lys
                180                 185                 190
Ala Met Gly Tyr Arg Val Leu Gly Ile Asp Gly Gly Pro Gly Lys Glu
                195                 200                 205
Glu Leu Phe Thr Ser Leu Gly Gly Glu Val Phe Ile Asp Phe Thr Lys
                210                 215                 220
Glu Lys Asp Ile Val Ser Ala Val Lys Ala Thr Asn Gly Gly Ala
225                 230                 235                 240
His Gly Ile Ile Asn Val Ser Val Ser Glu Ala Ala Ile Glu Ala Ser
                245                 250                 255
Thr Arg Tyr Cys Arg Ala Asn Gly Thr Val Val Leu Val Gly Leu Pro
                260                 265                 270
Ala Gly Ala Lys Cys Ser Ser Asp Val Phe Asn His Val Val Lys Ser
                275                 280                 285
Ile Ser Ile Val Gly Ser Tyr Val Gly Asn Arg Ala Asp Thr Arg Glu
                290                 295                 300
Ala Leu Asp Phe Phe Ala Arg Gly Leu Val Lys Ser Pro Ile Lys Val
305                 310                 315                 320
Val Gly Leu Ser Ser Leu Pro Glu Ile Tyr Glu Lys Met Glu Lys Gly
                325                 330                 335
Gln Ile Ala Gly Arg Tyr Val Val Asp Thr Ser Lys
                340                 345
```

<210> SEQ ID NO 74
<211> LENGTH: 30
<212> TYPE: DNA
<213> ORGANISM: Artificial
<220> FEATURE:
<223> OTHER INFORMATION: Synthetic DNA

<400> SEQUENCE: 74
tttgtttgtt tatgtgtgtt tattcgaaac                              30

<210> SEQ ID NO 75
<211> LENGTH: 41
<212> TYPE: DNA
<213> ORGANISM: Artificial
<220> FEATURE:
<223> OTHER INFORMATION: Synthetic DNA

<400> SEQUENCE: 75
tttgtttgtt tatgtgtgtt tattcgaaac taagttcttg g    41

<210> SEQ ID NO 76
<211> LENGTH: 25
<212> TYPE: DNA
<213> ORGANISM: Artificial
<220> FEATURE:
<223> OTHER INFORMATION: Synthetic DNA

<400> SEQUENCE: 76
cttaagacag gcccctttc ctttg    25

<210> SEQ ID NO 77
<211> LENGTH: 27
<212> TYPE: DNA
<213> ORGANISM: Artificial
<220> FEATURE:
<223> OTHER INFORMATION: Synthetic DNA

<400> SEQUENCE: 77
caatgaggag tgattttaca caaaaag    27

<210> SEQ ID NO 78
<211> LENGTH: 18
<212> TYPE: DNA
<213> ORGANISM: Artificial
<220> FEATURE:
<223> OTHER INFORMATION: Synthetic DNA

<400> SEQUENCE: 78
tcgctcgcag ccacgggt    18

<210> SEQ ID NO 79
<211> LENGTH: 26
<212> TYPE: DNA
<213> ORGANISM: Artificial
<220> FEATURE:
<223> OTHER INFORMATION: Synthetic DNA

<400> SEQUENCE: 79
tagcgttgaa tgttagcgtc aacaac    26

<210> SEQ ID NO 80
<211> LENGTH: 21
<212> TYPE: DNA
<213> ORGANISM: Artificial
<220> FEATURE:
<223> OTHER INFORMATION: Synthetic DNA

<400> SEQUENCE: 80
aggcaagtgc acaaacaata c    21

<210> SEQ ID NO 81
<211> LENGTH: 40
<212> TYPE: DNA
<213> ORGANISM: Artificial
<220> FEATURE:
<223> OTHER INFORMATION: Synthetic DNA

<400> SEQUENCE: 81
acgacattac tatatatata ataggaag catttaatag    40

<210> SEQ ID NO 82
<211> LENGTH: 24

-continued

<212> TYPE: DNA
<213> ORGANISM: Artificial
<220> FEATURE:
<223> OTHER INFORMATION: Synthetic DNA

<400> SEQUENCE: 82
ctggatagag cctcatcgtt acac                                          24

<210> SEQ ID NO 83
<211> LENGTH: 20
<212> TYPE: DNA
<213> ORGANISM: Artificial
<220> FEATURE:
<223> OTHER INFORMATION: Synthetic DNA

<400> SEQUENCE: 83
agccatcgca ctgtaccatg                                               20

<210> SEQ ID NO 84
<211> LENGTH: 20
<212> TYPE: DNA
<213> ORGANISM: Artificial
<220> FEATURE:
<223> OTHER INFORMATION: Synthetic DNA

<400> SEQUENCE: 84
ctatgggact tccgggaaac                                               20

<210> SEQ ID NO 85
<211> LENGTH: 20
<212> TYPE: DNA
<213> ORGANISM: Artificial
<220> FEATURE:
<223> OTHER INFORMATION: Synthetic DNA

<400> SEQUENCE: 85
gagggttggg cattcatcag                                               20

<210> SEQ ID NO 86
<211> LENGTH: 46
<212> TYPE: DNA
<213> ORGANISM: Artificial
<220> FEATURE:
<223> OTHER INFORMATION: Synthetic DNA

<400> SEQUENCE: 86
taacattcaa cgctatgtgt attacgatat agttaatagt tgatag                  46

<210> SEQ ID NO 87
<211> LENGTH: 40
<212> TYPE: DNA
<213> ORGANISM: Artificial
<220> FEATURE:
<223> OTHER INFORMATION: Synthetic DNA

<400> SEQUENCE: 87
acataaacaa acaaaatgtc tatcccagaa actcaaaaag                         40

<210> SEQ ID NO 88
<211> LENGTH: 39
<212> TYPE: DNA
<213> ORGANISM: Artificial
<220> FEATURE:
<223> OTHER INFORMATION: Synthetic DNA

<400> SEQUENCE: 88
aatcactcct cattgttgtc ctctgaggac ataaaatac                               39

<210> SEQ ID NO 89
<211> LENGTH: 28
<212> TYPE: DNA
<213> ORGANISM: Artificial
<220> FEATURE:
<223> OTHER INFORMATION: Synthetic DNA

<400> SEQUENCE: 89
ttgtcctctg aggacataaa atacacac                                          28

<210> SEQ ID NO 90
<211> LENGTH: 36
<212> TYPE: DNA
<213> ORGANISM: Artificial
<220> FEATURE:
<223> OTHER INFORMATION: Synthetic DNA

<400> SEQUENCE: 90
acataagaga tccgcgcgcc tcgttcagaa tgacac                                 36

<210> SEQ ID NO 91
<211> LENGTH: 35
<212> TYPE: DNA
<213> ORGANISM: Artificial
<220> FEATURE:
<223> OTHER INFORMATION: Synthetic DNA

<400> SEQUENCE: 91
gtcctcagag gacaacgttt taagagcttg gtgag                                  35

<210> SEQ ID NO 92
<211> LENGTH: 35
<212> TYPE: DNA
<213> ORGANISM: Artificial
<220> FEATURE:
<223> OTHER INFORMATION: Synthetic DNA

<400> SEQUENCE: 92
cgtggctgcg agcgacgttt taagagcttg gtgag                                  35

<210> SEQ ID NO 93
<211> LENGTH: 35
<212> TYPE: DNA
<213> ORGANISM: Artificial
<220> FEATURE:
<223> OTHER INFORMATION: Synthetic DNA

<400> SEQUENCE: 93
gcggatctct tatgtcttta cgatttatag ttttc                                  35

<210> SEQ ID NO 94
<211> LENGTH: 35
<212> TYPE: DNA
<213> ORGANISM: Artificial
<220> FEATURE:
<223> OTHER INFORMATION: Synthetic DNA

<400> SEQUENCE: 94
atatcgtaat acacacgttt taagagcttg gtgag                                  35

<210> SEQ ID NO 95
<211> LENGTH: 38
<212> TYPE: DNA
<213> ORGANISM: Artificial

<220> FEATURE:
<223> OTHER INFORMATION: Synthetic DNA

<400> SEQUENCE: 95
tgtgtattac gatatagtta atagttgata gttgattg             38

<210> SEQ ID NO 96
<211> LENGTH: 38
<212> TYPE: DNA
<213> ORGANISM: Artificial
<220> FEATURE:
<223> OTHER INFORMATION: Synthetic DNA

<400> SEQUENCE: 96
ggggcctgtc ttaagcttat ttagaagtgt caacaacg             38

<210> SEQ ID NO 97
<211> LENGTH: 33
<212> TYPE: DNA
<213> ORGANISM: Artificial
<220> FEATURE:
<223> OTHER INFORMATION: Synthetic DNA

<400> SEQUENCE: 97
taacattcaa cgctactgca ggaattcgat atc                  33

<210> SEQ ID NO 98
<211> LENGTH: 55
<212> TYPE: DNA
<213> ORGANISM: Artificial
<220> FEATURE:
<223> OTHER INFORMATION: Synthetic DNA

<400> SEQUENCE: 98
acataaacaa acaaagcgaa tttcttatga tttatgattt ttattattaa ataag    55

<210> SEQ ID NO 99
<211> LENGTH: 20
<212> TYPE: DNA
<213> ORGANISM: Artificial
<220> FEATURE:
<223> OTHER INFORMATION: Synthetic DNA

<400> SEQUENCE: 99
ccaactgtcc tcacgctgac                                 20

<210> SEQ ID NO 100
<211> LENGTH: 37
<212> TYPE: DNA
<213> ORGANISM: Artificial
<220> FEATURE:
<223> OTHER INFORMATION: Synthetic DNA

<400> SEQUENCE: 100
tttgtgcact tgcctgcgga tctcttatgt ctttacg              37

<210> SEQ ID NO 101
<211> LENGTH: 37
<212> TYPE: DNA
<213> ORGANISM: Artificial
<220> FEATURE:
<223> OTHER INFORMATION: Synthetic DNA

<400> SEQUENCE: 101
tgaggctcta tccagtgaca ccgattattt aaagctg              37

```
<210> SEQ ID NO 102
<211> LENGTH: 36
<212> TYPE: DNA
<213> ORGANISM: Artificial
<220> FEATURE:
<223> OTHER INFORMATION: Synthetic DNA

<400> SEQUENCE: 102
tacagtgcga tggctctttg ccttcgttta tcttgc                            36

<210> SEQ ID NO 103
<211> LENGTH: 26
<212> TYPE: DNA
<213> ORGANISM: Artificial
<220> FEATURE:
<223> OTHER INFORMATION: Synthetic DNA

<400> SEQUENCE: 103
cctcattgct gcaggaattc gatatc                                       26

<210> SEQ ID NO 104
<211> LENGTH: 28
<212> TYPE: DNA
<213> ORGANISM: Artificial
<220> FEATURE:
<223> OTHER INFORMATION: Synthetic DNA

<400> SEQUENCE: 104
cctgcagcaa tgaggagtga ttttacac                                     28

<210> SEQ ID NO 105
<211> LENGTH: 49
<212> TYPE: DNA
<213> ORGANISM: Artificial
<220> FEATURE:
<223> OTHER INFORMATION: Synthetic DNA

<400> SEQUENCE: 105
atatagtaat gtcgttgtgt attacgatat agttaatagt tgatagttg              49
```